US010674998B2

(12) United States Patent
Morimoto

(10) Patent No.: US 10,674,998 B2
(45) Date of Patent: Jun. 9, 2020

(54) ULTRASONIC ENDOSCOPE AND METHOD OF MANUFACTURING THE SAME

(71) Applicant: FUJIFILM Corporation, Tokyo (JP)

(72) Inventor: Yasuhiko Morimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 662 days.

(21) Appl. No.: 15/344,879

(22) Filed: Nov. 7, 2016

(65) Prior Publication Data
US 2017/0128044 A1    May 11, 2017

(30) Foreign Application Priority Data

Nov. 10, 2015  (JP) .................................. 2015-220042

(51) Int. Cl.
*A61B 8/14*      (2006.01)
*A61B 8/00*      (2006.01)
(Continued)

(52) U.S. Cl.
CPC .............. *A61B 8/445* (2013.01); *A61B 1/018* (2013.01); *A61B 8/12* (2013.01); *A61B 8/4494* (2013.01); *G10K 11/30* (2013.01)

(58) Field of Classification Search
None
See application file for complete search history.

(56) References Cited

U.S. PATENT DOCUMENTS

| | | | |
|---|---|---|---|
| 4,404,315 A | | 9/1983 | Tsukagoshi et al. |
| 6,149,598 A | * | 11/2000 | Tanaka ..................... A61B 8/12 600/437 |

(Continued)

FOREIGN PATENT DOCUMENTS

| | | |
|---|---|---|
| JP | 5-18509 U | 3/1993 |
| JP | 6-335481 A | 12/1994 |

(Continued)

OTHER PUBLICATIONS

Japanese Office Action dated Dec. 14, 2018, for corresponding Japanese Application No. 2015-220042, with an English translation.

(Continued)

*Primary Examiner* — Joel F Brutus
(74) *Attorney, Agent, or Firm* — Birch, Stewart, Kolasch & Birch, LLP

(57) ABSTRACT

The present invention provides an ultrasonic endoscope in which the position of an ultrasonic oscillator can be easily adjusted with respect to a surgical-tool guide opening provided to a leading end part body of an insertion unit, and a method of manufacturing the ultrasonic endoscope. According to the present invention, an ultrasonic oscillator can be positioned with respect to and temporarily fixed to an ultrasonic-oscillator housing part by using spacers and or protrusions. With this configuration, in an ultrasonic endoscope according to the present invention, the position of the ultrasonic oscillator can be adjusted with respect to the ultrasonic-oscillator housing part by using the spacers or the protrusions. Accordingly, the position of the ultrasonic oscillator can be adjusted with respect to a surgical-tool guide opening provided to a distal end part body of an insertion unit.

16 Claims, 14 Drawing Sheets

(51) Int. Cl.
*A61B 1/018* (2006.01)
*A61B 8/12* (2006.01)
*G10K 11/30* (2006.01)

(56) References Cited

U.S. PATENT DOCUMENTS

| | | | |
|---|---|---|---|
| 2002/0122246 A1* | 9/2002 | Tearney | A61B 1/00096 359/368 |
| 2007/0167814 A1* | 7/2007 | Wakabayashi | A61B 8/12 600/459 |
| 2007/0266792 A1* | 11/2007 | Oosawa | A61B 8/12 73/649 |
| 2009/0234233 A1* | 9/2009 | Nagano | A61B 8/12 600/462 |
| 2009/0253955 A1 | 10/2009 | Akiba | |
| 2014/0058269 A1 | 2/2014 | Irie | |
| 2016/0183914 A1 | 6/2016 | Fujimura | |

FOREIGN PATENT DOCUMENTS

| | | |
|---|---|---|
| JP | 9-75345 A | 3/1997 |
| JP | 2002-113005 A | 4/2002 |
| JP | 2007-68563 A | 3/2007 |
| JP | 2013-27695 A | 2/2013 |
| WO | WO 2015/053044 A1 | 4/2015 |

OTHER PUBLICATIONS

Extended European Search Report dated Jun. 26, 2017, issued in related European Patent Application No. 16197600.6.
European Office Action, dated Mar. 20, 2018, for corresponding European Application No. 16197688.1.
Extended European Search Report, dated Mar. 2, 2017, for European Application No. 16197688.1.
Partial European Search Report, dated Mar. 13, 2017, for European Application No. 16197600.6.
Japanese Office Action for corresponding Japanese Application No. 2015-220042, dated Jul. 8, 2019, with English translation.
U.S. Office Action, dated Oct. 16, 2019, for U.S. Appl. No. 15/341,527.

* cited by examiner

ULTRASONIC ENDOSCOPE AND METHOD OF MANUFACTURING THE SAME

CROSS-REFERENCE TO RELATED APPLICATIONS

The present application claims priority under 35 U.S.C. § 119 to Japanese Patent Application No. 2015-220042, filed on Nov. 10, 2015. The above application is hereby expressly incorporated by reference, in its entirety, into the present application.

BACKGROUND OF THE INVENTION

Field of the Invention

The present invention relates to an ultrasonic endoscope, and particularly relates to an ultrasonic endoscope including an ultrasonic observation unit provided to a distal end part body of an insertion unit, and a method of manufacturing the same.

Description of the Related Art

Recently, an ultrasonic endoscope has been used in clinical practice that allows observation of the state of the inside of a subject body by irradiating the inside of the body with ultrasonic waves and receiving the reflected waves for imaging.

Such an ultrasonic endoscope includes an ultrasonic probe (ultrasonic observation unit) provided to a distal end rigid part at the distal end of the insertion unit inserted into the inside of the body as disclosed in, for example, Japanese Patent Application Laid-Open No. 2002-113005. Typically, the ultrasonic probe includes, for example, an acoustic lens, a piezoelectric element, and a backing material, and is fixed to an ultrasonic-oscillator housing part provided to the distal end rigid part. The ultrasonic probe transmits and receives ultrasonic waves toward and from an observation region inside the body so as to acquire a signal for generating an ultrasonic image.

The distal end rigid part is provided with a surgical-tool guide opening on a proximal end side thereof. The surgical-tool guide opening is communicated with a surgical tool channel arranged inside the insertion unit, and a surgical tool inserted into the surgical tool channel is guided out of the surgical-tool guide opening. This configuration allows the ultrasonic observation unit to acquire the position of the surgical tool during an ultrasonic observation.

SUMMARY OF THE INVENTION

The surgical tool guided out of the surgical-tool guide opening needs to be accurately guided into an ultrasonic observation region to achieve a favorable ultrasonic observation using the ultrasonic endoscope, which requires a high accuracy of positioning the ultrasonic probe with respect to the surgical-tool guide opening.

However, Japanese Patent Application Laid-Open No. 2002-113005 provides no consideration on the above-described problem, and no means for solving the problem.

The following describes in detail the structure of an ultrasonic endoscope disclosed in Japanese Patent Application Laid-Open No. 2002-113005. An ultrasonic probe of the ultrasonic endoscope of Japanese Patent Application Laid-Open No. 2002-113005 is provided in an opening (ultrasonic-oscillator housing part) of an exterior case (distal end part body) provided to a distal end of a distal end rigid part thereof. The ultrasonic probe includes an acoustic lens, a second acoustic matching layer, a first acoustic matching layer, a piezoelectric element, and a backing material stacked on an outer surface in this order. The piezoelectric element is surrounded by a backing frame, and this backing frame is filled with the backing material, serving as a backing unit. The backing frame is engaged with an exterior member, and then this exterior member is fitted into the opening (ultrasonic-oscillator housing part) and bonded thereto. With this configuration, the ultrasonic probe is fixed to the opening (ultrasonic-oscillator housing part).

Since the ultrasonic endoscope of Japanese Patent Application Laid-Open No. 2002-113005 has the structure that the exterior member engaged with the backing frame is bonded to the opening (ultrasonic-oscillator housing part) in a simple manner, Japanese Patent Application Laid-Open No. 2002-113005 provides no consideration on adjustment of the position of the ultrasonic probe with respect to the surgical-tool guide opening, and provides no device to accurately and easily adjust the position. Thus, in the ultrasonic endoscope of Japanese Patent Application Laid-Open No. 2002-113005, the position of the exterior member is likely to shift with respect to the opening (ultrasonic-oscillator housing part). This positional shift degrades the accuracy of positioning the ultrasonic probe with respect to the surgical-tool guide opening, which indicates that the structure is unsuitable for performing a favorable ultrasonic observation.

The present invention is intended to solve such problems, and it is an object of the present invention to provide an ultrasonic endoscope in which the position of an ultrasonic oscillator can easily adjusted with respect to a surgical-tool guide opening provided to a distal end part body of an insertion unit, and a method of manufacturing the ultrasonic endoscope.

To achieve the object of the present invention, an ultrasonic endoscope according to the present invention includes an insertion unit inserted into an inside of the body, a distal end part body provided to a distal end of the insertion unit and provided with a surgical-tool guide opening, an ultrasonic observation unit provided to the distal end part body, an ultrasonic oscillator provided to the ultrasonic observation unit and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element, an ultrasonic-oscillator housing part provided to the distal end part body, covering the side surfaces and the bottom surface of the ultrasonic oscillator, and housing the ultrasonic oscillator, a spacer provided between the ultrasonic oscillator and the ultrasonic-oscillator housing part, and an acoustic lens covering the observation surface of the ultrasonic oscillator and the spacer and adhered to the ultrasonic-oscillator housing part.

To achieve the object of the present invention, an ultrasonic endoscope according to the present invention includes an insertion unit inserted into an inside of the body, a distal end part body provided to a distal end of the insertion unit and provided with a surgical-tool guide opening, an ultrasonic observation unit provided to the distal end part body, an ultrasonic oscillator provided to the ultrasonic observation unit and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element, an ultrasonic-oscillator housing part provided to the distal end part body, covering the side surfaces and the bottom surface of the ultrasonic oscillator, and housing the ultrasonic oscillator, a protrusion provided to at least one of the ultrasonic oscillator and the ultrasonic-oscillator housing part, and an acoustic lens covering the observation surface of the ultrasonic oscillator and the protrusion and adhered to the ultrasonic-oscillator housing part.

According to the present invention, the position of the ultrasonic oscillator can be adjusted with respect to the ultrasonic-oscillator housing part through the spacer or the protrusion, and thus the position of the ultrasonic oscillator can be easily adjusted with respect to the surgical-tool guide opening provided to the distal end part body of the insertion unit. With this configuration, the ultrasonic endoscope according to the present invention allows a surgical tool to be accurately guided into an ultrasonic observation region, thereby achieving a favorable ultrasonic observation.

The acoustic lens according to the present invention covers the observation surface of the ultrasonic oscillator, and the spacer or the protrusion, and is adhered to the ultrasonic-oscillator housing part. In other words, a gap between the ultrasonic oscillator and the ultrasonic-oscillator housing part is sealed by part of the acoustic lens without using sealing agent.

In one aspect of the present invention, it is preferable that the spacer has a uniform thickness in a direction normal to a surface of the spacer, which is in contact with a corresponding one of the side surfaces of the ultrasonic oscillator when the ultrasonic oscillator is housed in the ultrasonic-oscillator housing part.

In another aspect of the present invention, it is preferable that the protrusion has a uniform thickness in a direction normal to a surface of the protrusion, which is in contact with a corresponding one of the side surfaces of the ultrasonic oscillator when the ultrasonic oscillator is housed in the ultrasonic-oscillator housing part.

According to one aspect of the present invention, the spacer or the protrusion has a uniform thickness, and thus the ultrasonic oscillator can be accurately provided to the ultrasonic-oscillator housing part. A preferable uniform thickness of the spacer or the protrusion is a uniform thickness that provides parallelism enough to keep, inside the ultrasonic observation region, a surgical tool guided through the surgical-tool guide opening and entering into the ultrasonic observation region of the ultrasonic oscillator from a proximal side end face of the observation region. The ultrasonic observation region when viewed from the surgical-tool guide opening includes a region narrowed in a direction intersecting with the longitudinal axis of the insertion unit. The uniform thickness that provides parallelism enough to keep the surgical tool inside the ultrasonic observation region through the spacer or the protrusion is such a uniform thickness that the parallelism of side surfaces parallel to the longitudinal axis of the insertion unit among the side surfaces of the ultrasonic oscillator with respect to the guide direction of the surgical tool can be provided through the spacer or the protrusion so as to keep the surgical tool inside the narrowed region.

In another aspect of the present invention, it is preferable that the spacer is provided between the ultrasonic-oscillator housing part and a side surface parallel to the longitudinal axis of the insertion unit among the side surfaces of the ultrasonic oscillator.

In another aspect of the present invention, it is preferable that the protrusion is provided between the ultrasonic-oscillator housing part and a side surface parallel to the longitudinal axis of the insertion unit among the side surfaces of the ultrasonic oscillator.

According to one aspect of the present invention, a constant gap can be held through the spacer or the protrusion between the ultrasonic-oscillator housing part and the side surface parallel to the longitudinal axis of the insertion unit among the side surfaces of the ultrasonic oscillator.

In another aspect of the present invention, it is preferable that the spacers are provided between the ultrasonic-oscillator housing part and two side surfaces parallel to the longitudinal axis of the insertion unit and facing to each other among the side surfaces of the ultrasonic oscillator, and that when the ultrasonic oscillator is housed in the ultrasonic-oscillator housing part, the spacers provided between the ultrasonic-oscillator housing part and the two side surfaces have thicknesses equal to each other, each thickness being measured in a direction normal to a surface of the spacer, which is in contact with a corresponding one of the side surfaces of the ultrasonic oscillator.

In another aspect of the present invention, it is preferable that the protrusion is provided to at least one of the ultrasonic-oscillator housing part and a first side surface as one of two side surfaces parallel to the longitudinal axis of the insertion unit and facing to each other among the side surfaces of the ultrasonic oscillator, and is provided to at least one of the ultrasonic-oscillator housing part and a second side surface as the other side surface, and that when the ultrasonic oscillator is housed in the ultrasonic-oscillator housing part, the protrusion provided to at least one of the ultrasonic-oscillator housing part and the first side surface and the protrusion provided to at least one of the ultrasonic-oscillator housing part and the second side surface have thicknesses equal to each other, each thickness being measured in a direction normal to a surface of the protrusion, which is in contact with a corresponding one of the first and second side surfaces of the ultrasonic oscillator.

According to one aspect of the present invention, the two side surfaces parallel to the longitudinal axis of the insertion unit and facing to each other among the side surfaces of the ultrasonic oscillator can be arranged in parallel to the longitudinal axis of the insertion unit through the spacers or the protrusions. In the aspect of the present invention, the thickness of a spacer or a protrusion in a normal direction is such a thickness that achieves electrical insulation through the spacer or the protrusion and a small outer shape of the distal end part body. Thicknesses in the normal direction are said to be equal to each other with any variation in manufacturing the spacer or the protrusion.

In another aspect of the present invention, it is preferable that the spacer is provided between the ultrasonic-oscillator housing part and a side surface intersecting with the longitudinal axis of the insertion unit among the side surfaces of the ultrasonic oscillator.

In another aspect of the present invention, it is preferable that the protrusion is provided to at least one of the ultrasonic-oscillator housing part and a side surface intersecting with the longitudinal axis of the insertion unit among the side surfaces of the ultrasonic oscillator.

According to one aspect of the present invention, a constant gap can be held through the spacer or the protrusion between the ultrasonic-oscillator housing part and the side surface intersecting with the longitudinal axis of the insertion unit among the side surfaces of the ultrasonic oscillator.

In another aspect of the present invention, it is preferable that the spacers are provided between the ultrasonic-oscillator housing part and two side surfaces intersecting with the longitudinal axis of the insertion unit and facing to each other among the side surfaces of the ultrasonic oscillator, and that when the ultrasonic oscillator is housed in the ultrasonic-oscillator housing part, the spacers provided between the ultrasonic-oscillator housing part and the two side surfaces have thicknesses equal to each other, each thickness being measured in a direction normal to a surface of the spacer, which is in contact with a corresponding one of the side surfaces of the ultrasonic oscillator.

In another aspect of the present invention, it is preferable that the protrusion is provided to at least one of the ultrasonic-oscillator housing part and a third side surface as one of two side surfaces intersecting with the longitudinal axis of the insertion unit and facing to each other among the side surfaces of the ultrasonic oscillator, and is provided to at least one of the ultrasonic-oscillator housing part and a fourth side surface as the other side surface, and that when the ultrasonic oscillator is housed in the ultrasonic-oscillator housing part, the protrusion provided to at least one of the ultrasonic-oscillator housing part and the third side surface and the protrusion provided to at least one of the ultrasonic-oscillator housing part and the fourth side surface have thicknesses equal to each other, each thickness being measured in a direction normal to a surface of the protrusion, which is in contact with a corresponding one of the second and third side surfaces of the ultrasonic oscillator.

According to one aspect of the present invention, the two side surfaces intersecting with the longitudinal axis of the insertion unit and facing to each other among the side surfaces of the ultrasonic oscillator can be arranged in a direction intersecting with the longitudinal axis of the insertion unit through the spacers or the protrusions.

In another aspect of the present invention, it is preferable that the spacer is elastic in a thickness direction corresponding to in the normal direction.

In another aspect of the present invention, it is preferable that the protrusion is elastic in a thickness direction corresponding to the normal direction.

According to one aspect of the present invention, the spacer or the protrusion is elastic, and thus can cancel any error in the dimensions of the ultrasonic oscillator and the ultrasonic-oscillator housing part through elastic deformation thereof.

In another aspect of the present invention, it is preferable that the spacer is provided between the ultrasonic-oscillator housing part and the bottom surface of the ultrasonic oscillator.

In another aspect of the present invention, it is preferable that the protrusion is provided to at least one of the ultrasonic-oscillator housing part and the bottom surface of the ultrasonic oscillator.

According to one aspect of the present invention, the bottom surface of the ultrasonic oscillator can be supported with respect to the ultrasonic-oscillator housing part through the spacer or the protrusion.

In another aspect of the present invention, it is preferable that the ultrasonic endoscope further includes a wiring connection unit provided to the ultrasonic oscillator and connected with wiring for supplying a drive voltage to the ultrasonic oscillator, the wiring connection unit is provided in a central part of the bottom surface, and the spacer is provided in a peripheral part of the bottom surface.

In another aspect of the present invention, it is preferable that the ultrasonic endoscope further includes a wiring connection unit provided to the ultrasonic oscillator and connected with wiring for supplying a drive voltage to the ultrasonic oscillator, the wiring connection unit is provided in a central part of the bottom surface, and the protrusion is provided in a peripheral part of the bottom surface.

According to one aspect of the present invention, the spacer or the protrusion serves as a weir, thereby preventing melted resin of the acoustic lens from flowing into the wiring connection unit when the acoustic lens is shaped.

To achieve the object of the present invention, a method of manufacturing an ultrasonic endoscope according to the present invention is a method of manufacturing an ultrasonic endoscope including an insertion unit inserted into an inside of the body, a distal end part body provided to a distal end of the insertion unit and provided with a surgical-tool guide opening, an ultrasonic observation unit provided to the distal end part body, an ultrasonic oscillator provided to the ultrasonic observation unit and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element, and an ultrasonic-oscillator housing part provided to the distal end part body and housing the ultrasonic oscillator, the method including housing the ultrasonic oscillator in the ultrasonic-oscillator housing part, temporarily fixing the ultrasonic oscillator to the ultrasonic-oscillator housing part while an extended line of a center line of the surgical-tool guide opening is positioned in an observation region of the ultrasonic oscillator, and shaping an acoustic lens on the observation surface of the ultrasonic oscillator with fluid resin and filling a gap between the ultrasonic oscillator and the ultrasonic-oscillator housing part with the resin while temporarily fixing the ultrasonic oscillator.

According to the present invention, the position of the ultrasonic oscillator can be adjusted with respect to the surgical-tool guide opening provided to the distal end part body of the insertion unit.

The present invention provides an ultrasonic endoscope in which the position of an ultrasonic oscillator can be adjusted with respect to a surgical-tool guide opening provided to a distal end part body of an insertion unit, and a method of manufacturing the ultrasonic endoscope.

DETAILED DESCRIPTION OF THE PREFERRED EMBODIMENTS

Preferable embodiments of an ultrasonic endoscope according to the present invention and a method of manufacturing the ultrasonic endoscope will be described below in detail with reference to the accompanying drawings.

Figure 1:
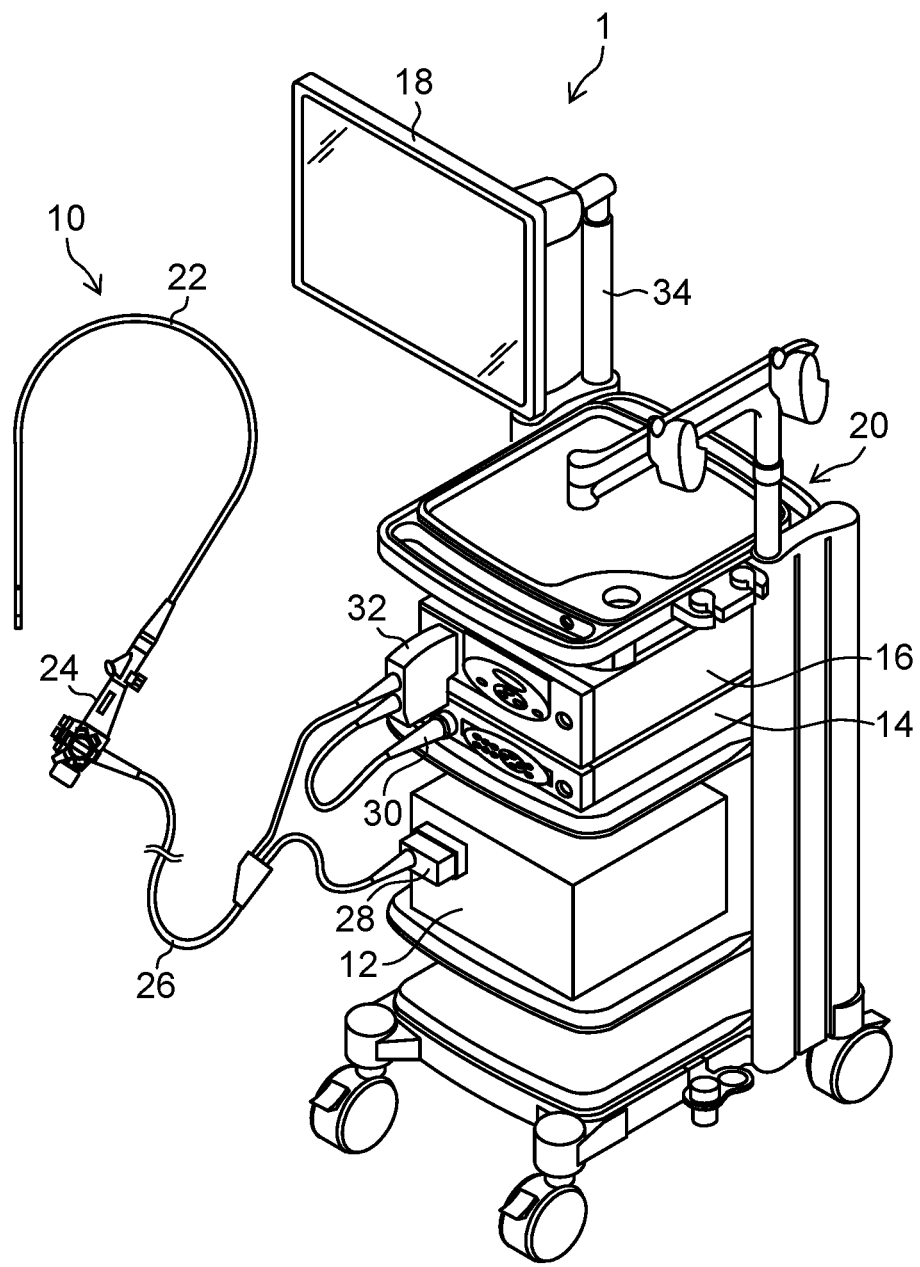
FIG. 1 is an entire configuration diagram of an ultrasonic examination system including an ultrasonic endoscope according to an embodiment.
Figure 2:
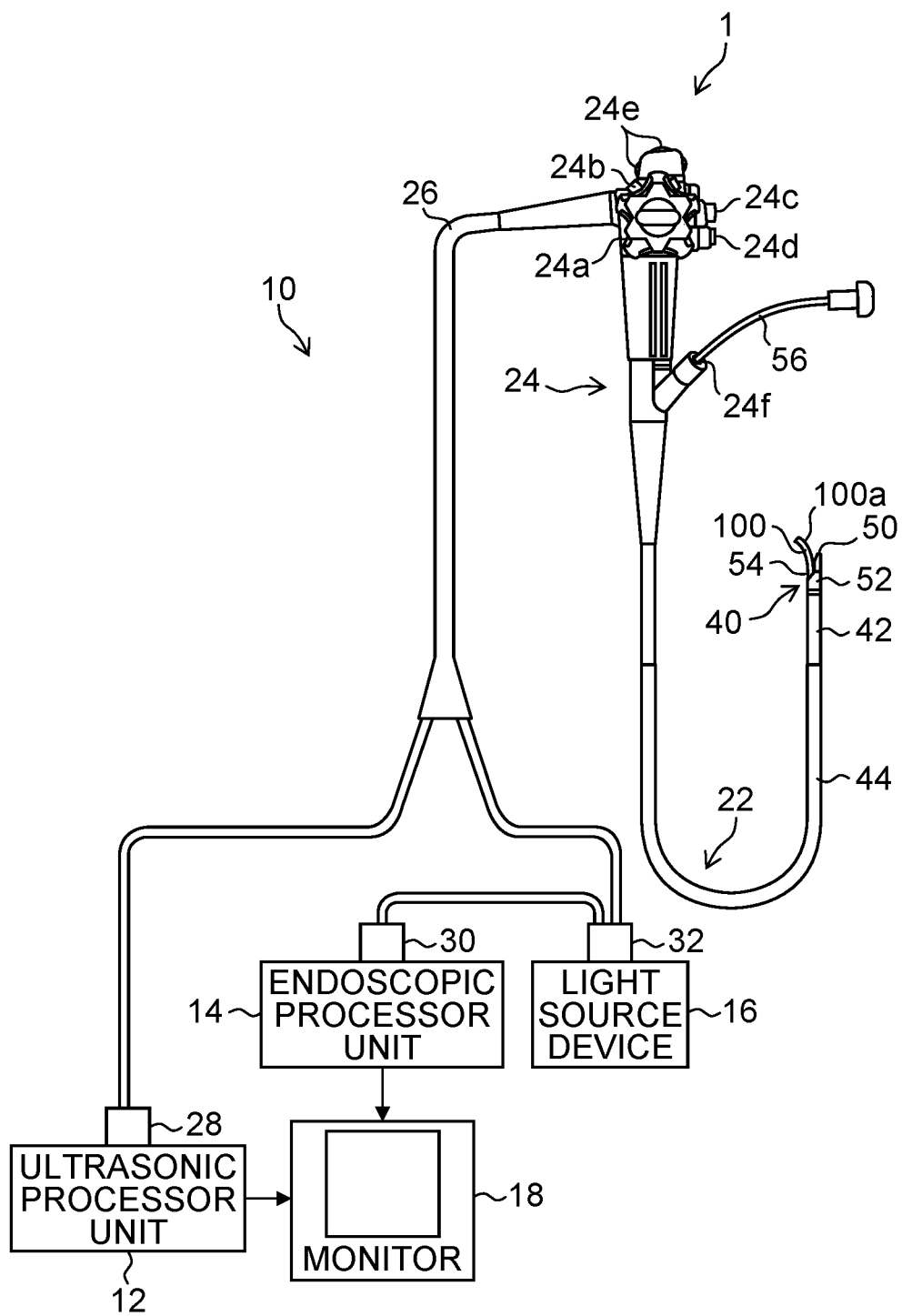
FIG. 2 is a block diagram illustrating the entire configuration of the ultrasonic examination system in FIG. 1.

FIG. 1 is an entire configuration diagram of an ultrasonic examination system 1 including an ultrasonic endoscope 10 according to the present embodiment. FIG. 2 is a block diagram of the entire configuration of the ultrasonic examination system 1 illustrated in FIG. 1.

[Ultrasonic Examination System 1]

The ultrasonic examination system 1 includes the ultrasonic endoscope 10 that captures an endoscopic image and an ultrasonic image of the inside of the body, an ultrasonic processor unit 12 that generates an ultrasonic image, an endoscopic processor unit 14 that generates an endoscopic image, a light source device 16 that supplies the ultrasonic endoscope 10 with illumination light that illuminates the inside of the body, and a monitor 18 that displays an endoscopic image and an ultrasonic image thereon.

[Ultrasonic Endoscope 10]

The ultrasonic endoscope 10 is a convex ultrasonic endoscope including an insertion unit 22 inserted into the inside of the body, an operating unit 24 provided continuously with a proximal end of the insertion unit 22, and a universal cord 26 a proximal end of which is connected with the operating unit 24. A distal end of the universal cord 26 is provided with a connector 28 connected with the ultrasonic processor unit 12, a connector 30 connected with the endoscopic processor unit 14, and a connector 32 connected with the light source device 16. The ultrasonic endoscope 10 is detachably connected with the ultrasonic processor unit 12, the endoscopic processor unit 14, and the light source device 16 through the respective connectors 28, 30, and 32.

The ultrasonic processor unit 12, the endoscopic processor unit 14, and the light source device 16 are loaded on a cart 20 with casters as illustrated in FIG. 1 and integrally moved. The monitor 18 is supported by a support 34 of the cart 20. The direction and height of a screen of the monitor 18 are adjusted through a rotation mechanism and a height adjusting mechanism (not illustrated) provided to the support 34.

<Insertion Unit 22>

As illustrated in FIG. 2, the insertion unit 22 includes a distal end rigid part 40 including a distal end part body 70 (refer to FIG. 3) made of a rigid material, a curved part 42 provided continuously with a proximal end side of the distal end rigid part 40, and a flexible part 44 having flexibility and a small diameter and a long length and coupling a proximal end side of the curved part 42 and a distal end of the operating unit 24, in this order from its distal end. In other words, the distal end of the insertion unit 22 is provided with the distal end part body 70. A surgical-tool guide opening 54 to be described later is formed in the distal end part body 70 (refer to FIG. 3).

Figure 3:
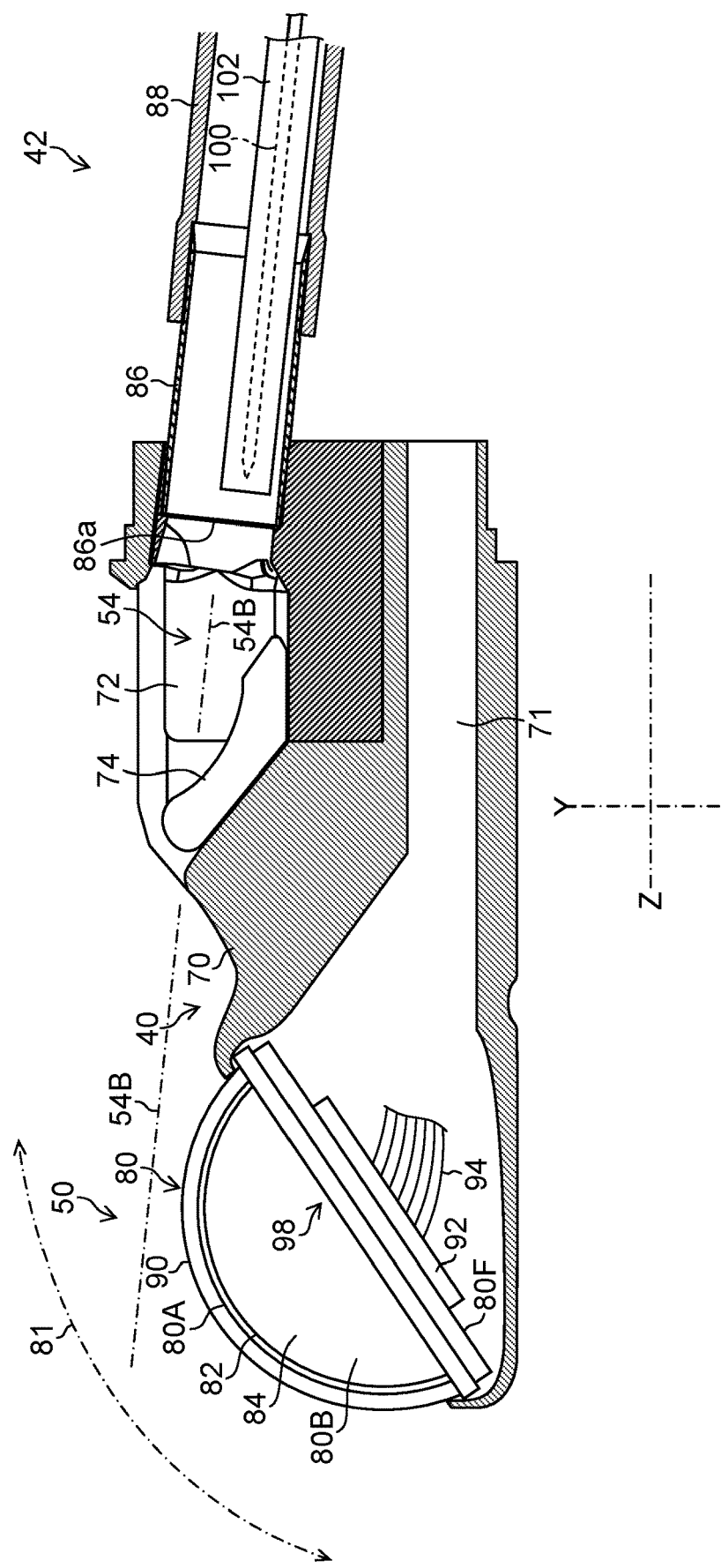
FIG. 3 is an enlarged sectional view illustrating a main part of a distal end structure of an insertion unit of the ultrasonic endoscope illustrated in FIG. 1.

FIG. 3 is a main-part enlarged sectional view illustrating a non-angled state of the insertion unit 22 of the ultrasonic endoscope 10 illustrated in FIG. 1.

A surgical-tool insertion tube 88 is arranged inside of the insertion unit 22 so as to guide a surgical tool including a puncture needle 100 and a sheath 102 to the surgical-tool guide opening 54. A proximal end of the surgical-tool insertion tube 88 is connected with a surgical-tool insertion opening 24f provided to the operating unit 24 illustrated in FIG. 2, whereas a distal end thereof is connected with a proximal end of a connecting pipe 86 (refer to FIG. 3) arranged at a coupling position of the distal end rigid part 40 and the curved part 42. The connecting pipe 86 is made of metal such as stainless steel, mounted on the distal end part body 70 such that a distal end thereof is communicated with the surgical-tool guide opening 54. The surgical-tool insertion tube 88 is made of, for example, polytetrafluoroethylene (PTFE).

As illustrated in FIG. 2, the distal end part body 70 (refer to FIG. 3) of the distal end rigid part 40 is provided with an ultrasonic observation unit 50, an endoscope observation unit 52, and the surgical-tool guide opening 54.

The ultrasonic observation unit 50 includes an ultrasonic oscillator including an observation surface through which ultrasonic waves are communicated as described later. The ultrasonic observation unit 50 acquires an ultrasonic signal for generating as an ultrasonic image, a topographic image of cellular tissue existing deeper than a wall of the body cavity.

The endoscope observation unit 52 includes, for example, components of an observation optical system and an illumination optical system and an image pickup element and a peripheral circuit thereof as described later. The endoscope observation unit 52 optically captures the surface of a wall of the body cavity so as to acquire an image signal for displaying an endoscopic image for observation.

As illustrated in FIG. 3, the surgical-tool guide opening 54 guides, into the inside of the body, a distal end (a distal end 100a of the puncture needle 100 in FIG. 2) of the surgical tool including the puncture needle 100 and the sheath 102 inserted into the surgical-tool insertion tube 88. The surgical-tool guide opening 54 is communicated with a distal end of the connecting pipe 86, and an elevator 74 that changes a direction in which the puncture needle 100 is guided is provided closer to the distal end of the connecting pipe 86.

Although embodiment exemplarily describes the surgical tool including the puncture needle 100 and the sheath 102, the present invention is not limited thereto but is applicable to other surgical tools such as forceps.

<Operating Unit 24>

As illustrated in FIG. 2, the operating unit 24 includes, for example, an angle knob 24a for curving the curved part 42 of the insertion unit 22 vertically and horizontally, an elevation lever 24b for standing up the elevator 74 (refer to FIG. 3), a suction button 24c for performing suction, an insufflation button 24d for performing air and water supply, and a plurality of operation members 24e for performing display switching of the monitor and instructions to freeze and release a display image. The surgical-tool insertion opening 24f for inserting various surgical tools into the surgical-tool insertion tube 88 (refer to FIG. 3) is provided as an extension closer to the distal end of the operating unit 24.

<Processor Unit and the Like>

The ultrasonic processor unit 12 transmits ultrasonic waves at a predetermined frequency from the observation surface toward an observation object by driving a piezoelectric element (to be described later) included in the ultrasonic observation unit 50. Then, the ultrasonic processor unit 12 receives, through the observation surface, ultrasonic waves reflected from the observation object and acquires, from the ultrasonic observation unit 50, an electric signal (ultrasonic signal) obtained from the received ultrasonic waves, and generates an image signal for an ultrasonic image by performing various kinds of signal processing on the electric signal.

The endoscopic processor unit 14 acquires the image signal transmitted from the image pickup element of the endoscope observation unit 52 of the ultrasonic endoscope 10 by performing drive control of the image pickup element, and generates an image signal for an endoscopic image by performing various kinds of signal processing on the image signal.

The light source device 16 supplies the illumination optical system with illumination light to be emitted from the illumination optical system of the distal end rigid part 40 for illuminating an observation view range of the endoscope observation unit 52.

The monitor 18 receives the image signals generated by the ultrasonic processor unit 12 and the endoscopic processor unit 14, and displays an ultrasonic image and an endoscopic image. In the display of these ultrasonic and endoscopic images, each of the images may be displayed on the monitor 18 in a switching manner as appropriate or both of the images may be simultaneously displayed on the monitor 18.

<Distal End Rigid Part 40>

FIGS. 4, 5, 6, and 7 are a perspective view, a plan view, a side view, and a front view of the distal end rigid part 40, respectively.

As illustrated in these diagrams, the distal end part body 70 of the distal end rigid part 40 is provided with the ultrasonic observation unit 50, the endoscope observation unit 52, and the surgical-tool guide opening 54 as described above.

<Ultrasonic Observation Unit 50>

As illustrated in FIG. 3, the ultrasonic observation unit 50 is provided to the distal end part body 70. The ultrasonic observation unit 50 is provided with an ultrasonic oscillator 80.

Figure 4:
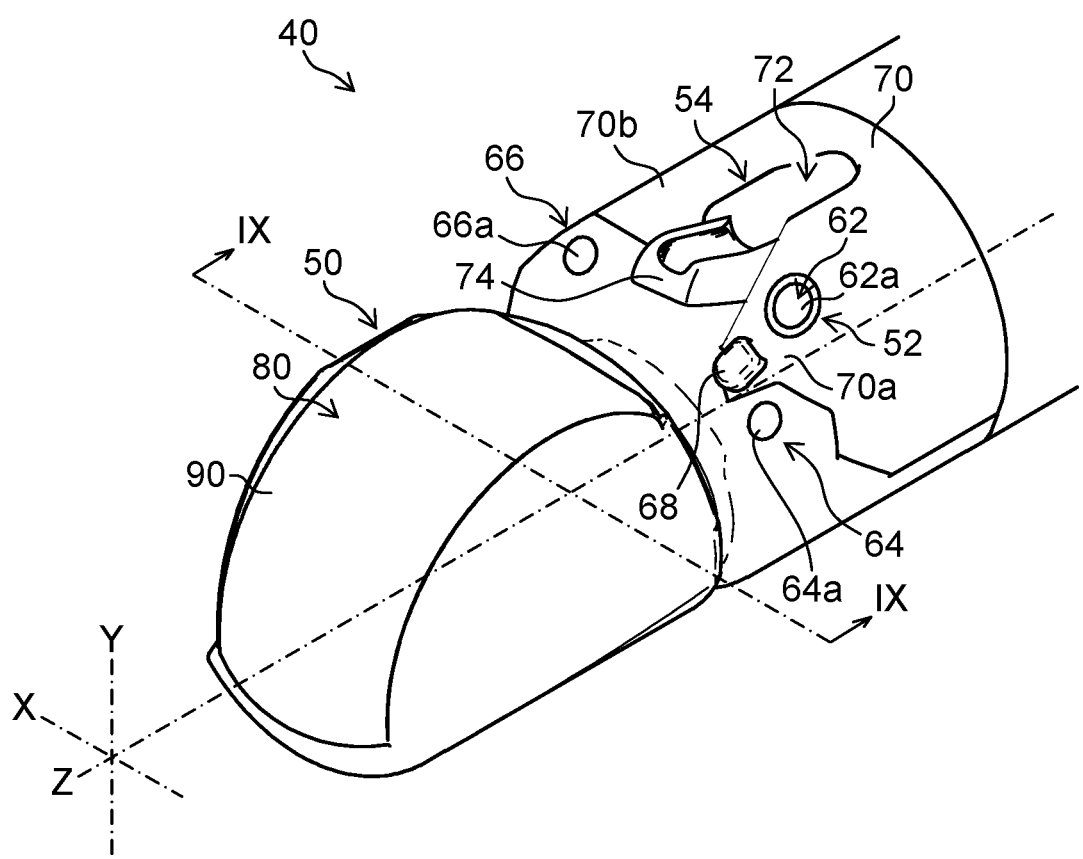
FIG. 4 is a perspective view of a distal end rigid part of the ultrasonic endoscope.
Figure 5:
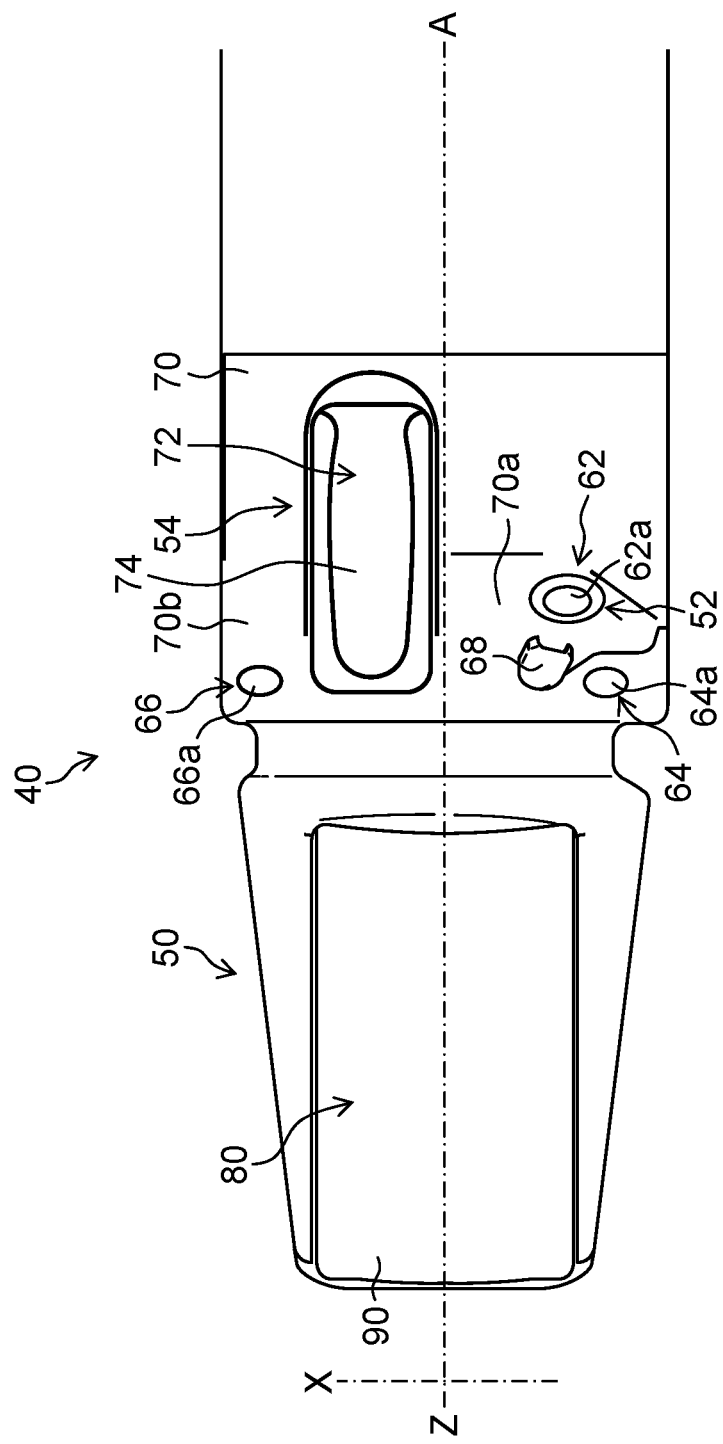
FIG. 5 is a plan view of the distal end rigid part of the ultrasonic endoscope.
Figure 6:
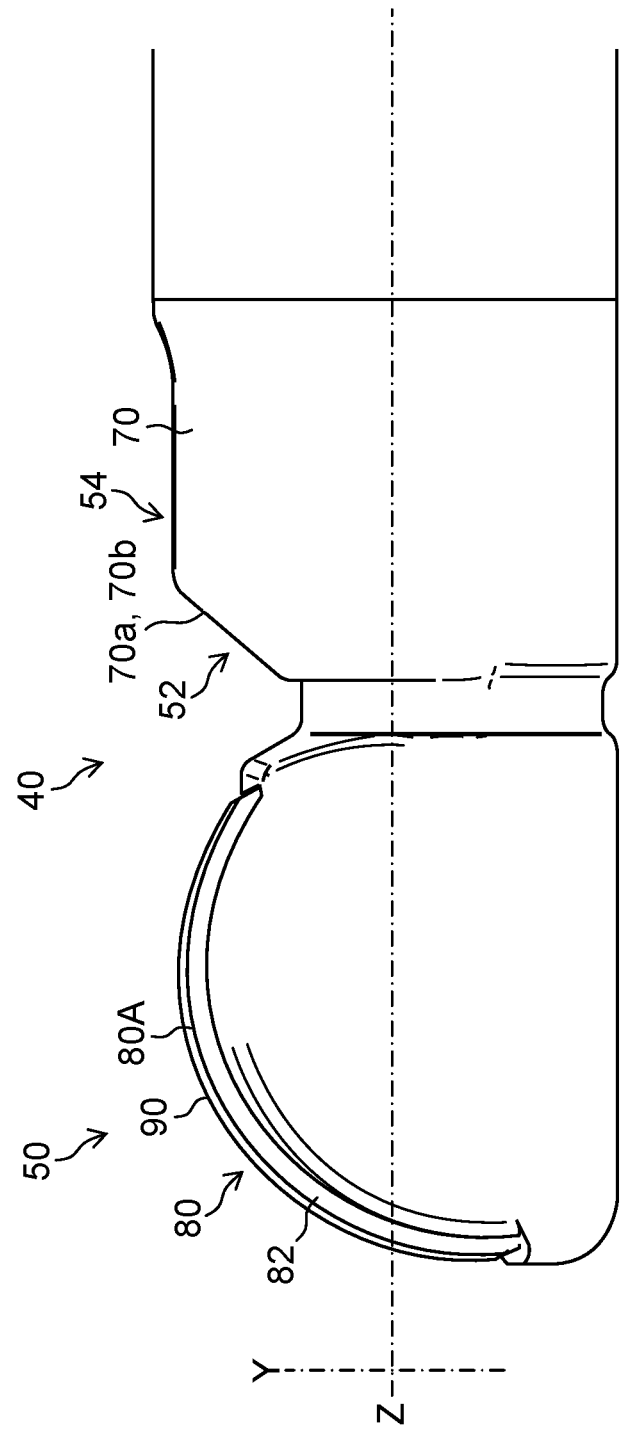
FIG. 6 is a side view of the distal end rigid part of the ultrasonic endoscope.
Figure 7:
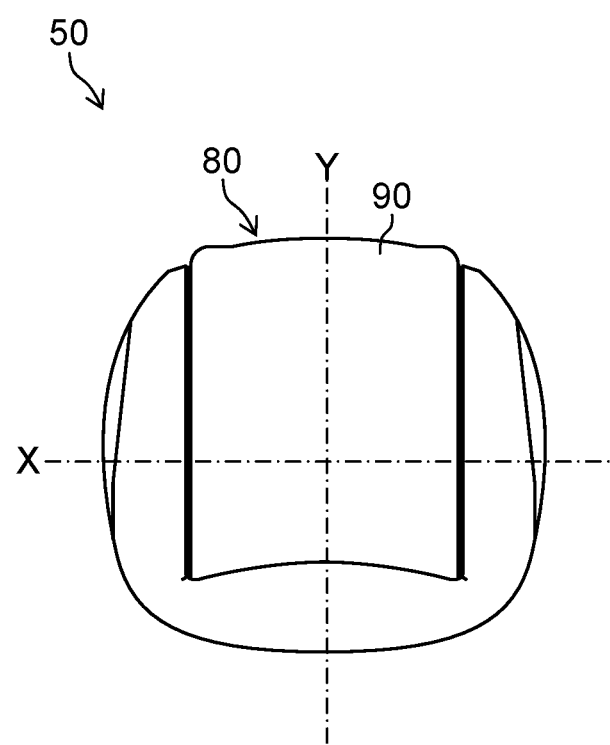
FIG. 7 is a front view of the distal end rigid part of the ultrasonic endoscope.
Figure 8:
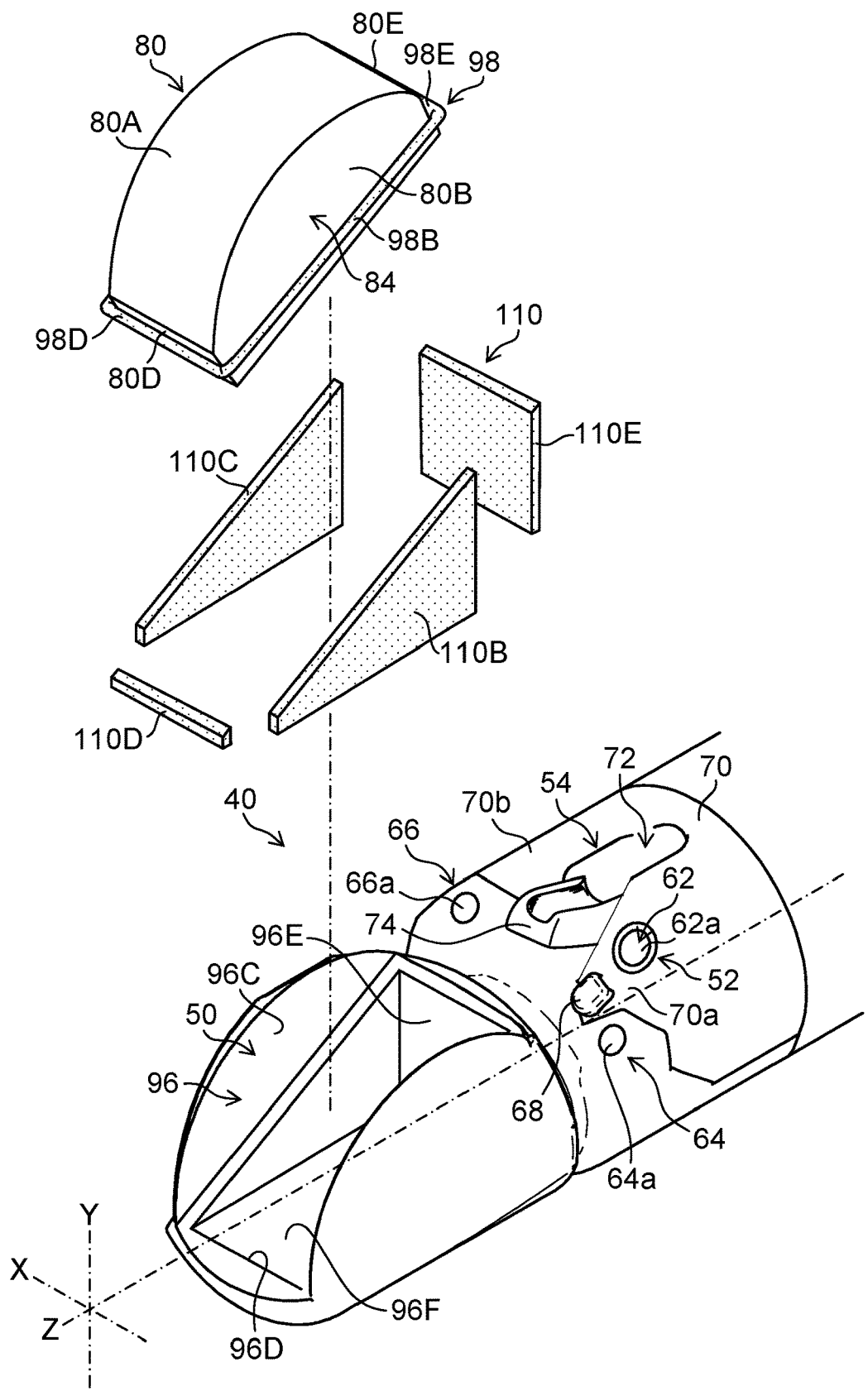
FIG. 8 is a diagram illustrating assembly of an ultrasonic oscillator to the distal end part body.
Figure 9:
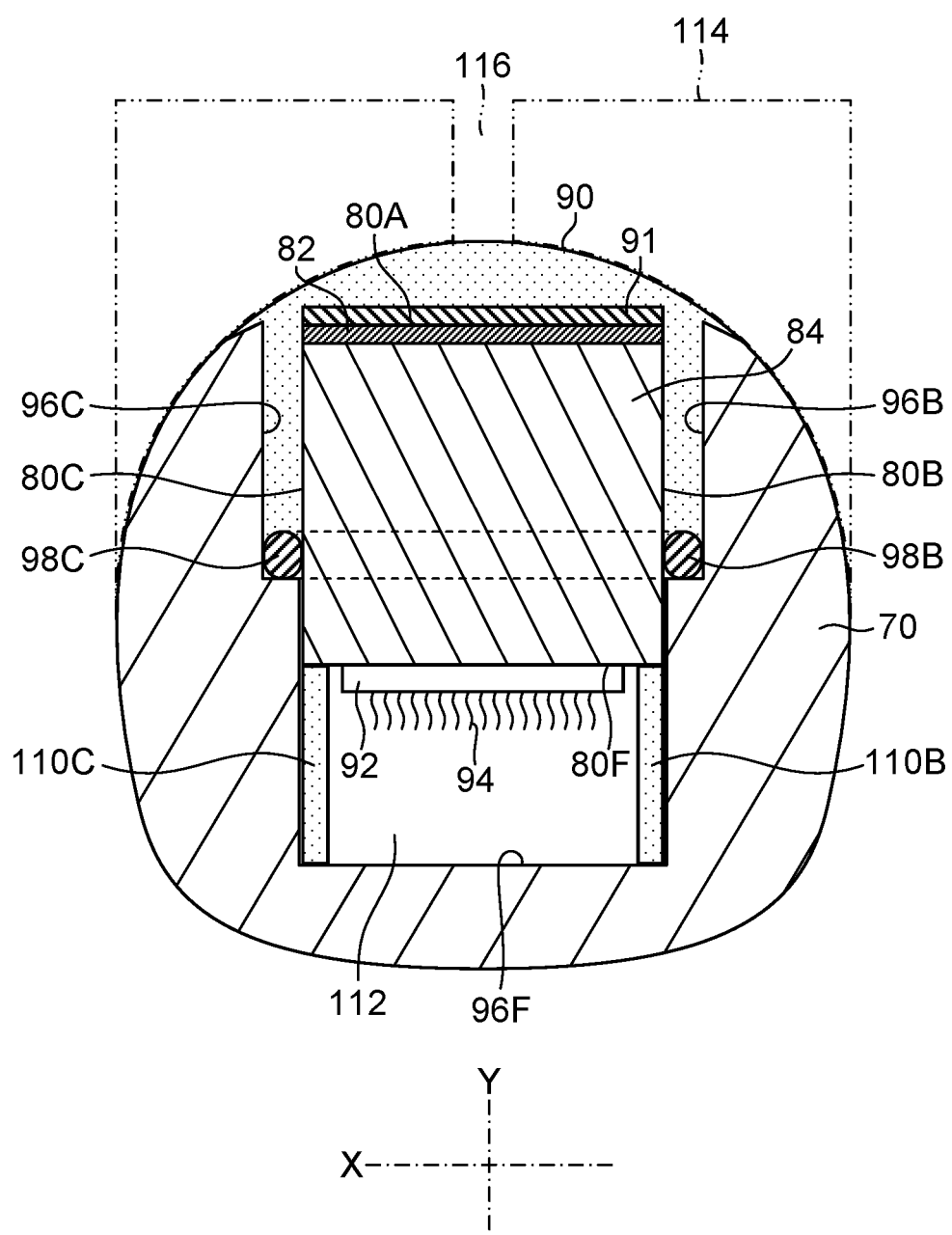
FIG. 9 is a sectional view of the distal end part body and the ultrasonic oscillator taken along line IX-IX in FIG. 4.
Figure 10:
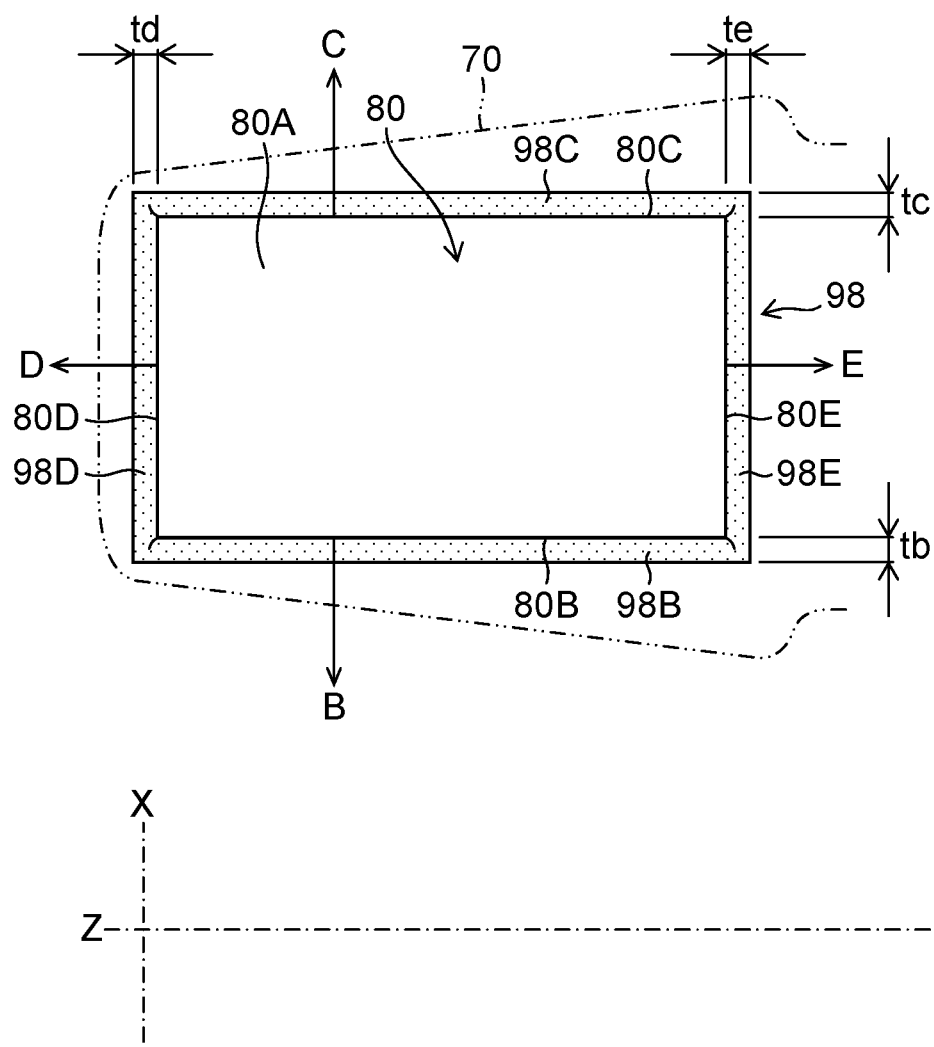
FIG. 10 is a plan view of the ultrasonic oscillator.

FIG. 8 is a diagram illustrating assembly of the ultrasonic oscillator 80 to the distal end part body 70, FIG. 9 is a sectional view of the distal end part body 70 and the ultrasonic oscillator 80 taken along line IX-IX in FIG. 4, and FIG. 10 is a plan view of the ultrasonic oscillator 80.

As illustrated in these diagrams, the ultrasonic oscillator 80 includes an observation surface 80A through which ultrasonic waves are communicated, four side surfaces 80B, 80C, 80D, and 80E adjacent to the observation surface 80A, a bottom surface 80F opposite to the observation surface 80A, a plurality of plate piezoelectric elements 82 provided closer to the observation surface 80A, and a backing material 84 provided to the bottom surfaces of the plurality of piezoelectric elements 82. The four side surfaces are side surfaces of the backing material 84 formed in a semi-cylinder. Among the side surfaces, the side surfaces 80B and 80C are two side surfaces parallel to a longitudinal axis Z of the insertion unit 22 and facing to each other, and the side surfaces 80D and 80E are two side surfaces intersecting with the longitudinal axis Z of the insertion unit 22 and facing to each other.

The plurality of piezoelectric elements 82 are arrayed in the direction of the longitudinal axis Z of the insertion unit 22. In other words, the plurality of piezoelectric elements 82 are arrayed from a position close to a distal end of the distal end rigid part 40 toward the proximal end side of the distal end rigid part 40, and their surfaces serve as the observation surface 80A through which ultrasonic waves are communicated. The observation surface 80A is shaped as an arc surface in the direction of the longitudinal axis Z, but is not limited to this shape, and may be shaped as a curved surface having a plurality of different curvatures. The observation surface 80A is provided, through an acoustic matching layer 91 (refer to FIG. 9), with an acoustic lens 90 for converging ultrasonic waves.

The plurality of piezoelectric elements 82 are each provided with an electrode (not illustrated), and the electrode is connected with a wiring connection unit 92 in FIG. 9 through a flexible printed board (not illustrated). The wiring connection unit 92 is provided in a central part of the bottom surface 80F of the ultrasonic oscillator 80, which is formed in a rectangle. The wiring connection unit 92 is connected with a plurality of narrow wires 94 for supplying a drive voltage to the plurality of piezoelectric elements 82, and these wires 94 are inserted into a wiring insertion hole 71 (refer to FIG. 3) of the distal end part body 70 and connected with the connector 28 in FIG. 2.

The ultrasonic observation unit 50 can perform ultrasonic electron scanning by supplying a drive voltage from the ultrasonic processor unit 12 to the plurality of piezoelectric elements 82 to sequentially drive the plurality of piezoelectric elements 82.

In FIGS. 3 to 10, an X axis is defined to be a horizontal axis in a transverse direction orthogonal to the longitudinal axis Z, and a Y axis is defined to be a vertical axis in the vertical direction.

The distal end part body 70 is provided with an ultrasonic-oscillator housing part 96 with an opening upper part as illustrated in FIG. 8. The ultrasonic-oscillator housing part 96 includes side surfaces 96B (refer to FIG. 9), 96C, 96D, and 96E and a bottom surface 96F covering the side surfaces 80B, 80C, 80D, and 80E and the bottom surface 80F of the ultrasonic oscillator 80, thereby housing the ultrasonic oscillator 80.

A spacer 98 is provided between the side surfaces 80B, 80C, 80D, and 80E of the ultrasonic oscillator 80 and the side surfaces 96B, 96C, 96D, and 96E of the ultrasonic-oscillator housing part 96. The position of the ultrasonic oscillator 80 is adjusted with respect to the ultrasonic-oscillator housing part 96 through the spacer 98, and the position of the ultrasonic oscillator 80 is adjusted with respect to the surgical-tool guide opening 54 (refer to FIG. 3) accordingly.

[Spacer 98]

The spacer 98 is a frame member formed as an integration of four spacers 98B, 98C, 98D, and 98E. The spacer 98B is provided between the side surface 80B of the ultrasonic oscillator 80 and the side surface 96B of the ultrasonic-oscillator housing part 96, the spacer 98C is provided between the side surface 80C of the ultrasonic oscillator 80 and the side surface 96C of the ultrasonic-oscillator housing part 96, the spacer 98D is provided between the side surface 80D of the ultrasonic oscillator 80 and the side surface 96D of the ultrasonic-oscillator housing part 96, and the spacer 98E is provided between the side surface 80E of the ultrasonic oscillator 80 and the side surface 96E of the ultrasonic-oscillator housing part 96.

In other words, an interval between the side surface 80B of the ultrasonic oscillator 80 and the side surface 96B of the ultrasonic-oscillator housing part 96 is accurately held by the spacer 98B, an interval between the side surface 80C of the ultrasonic oscillator 80 and the side surface 96C of the ultrasonic-oscillator housing part 96 is accurately held by the spacer 98C, an interval between the side surface 80D of the ultrasonic oscillator 80 and the side surface 96D of the ultrasonic-oscillator housing part 96 is accurately held by the spacer 98D, and an interval between the side surface 80E of the ultrasonic oscillator 80 and the side surface 96E of the ultrasonic-oscillator housing part 96 is accurately held by the spacer 98E. This configuration allows the position of the ultrasonic oscillator 80 to be accurately and easily adjusted with respect to the ultrasonic-oscillator housing part 96, and allows the position of the ultrasonic oscillator 80 to be accurately and easily adjusted with respect to the surgical-tool guide opening 54 (refer to FIG. 3).

Although the present embodiment describes the example in which the spacer 98 is provided to the ultrasonic oscillator 80, the spacer 98 may be provided to the ultrasonic-oscillator housing part 96. Although the present embodiment exemplarily describes the four spacers 98B, 98C, 98D, and 98E, at least one spacer is needed. The spacer is provided independently from the ultrasonic oscillator 80 and the ultrasonic-oscillator housing part 96, and attached to the ultrasonic oscillator 80 or the ultrasonic-oscillator housing part 96. The spacer is conceptually different from a protrusion to be described later in this point. Specifically, the protrusion is formed integrally with at least one of the ultrasonic oscillator 80 or the ultrasonic-oscillator housing part 96.

It is preferable that when the ultrasonic oscillator 80 is housed in the ultrasonic-oscillator housing part 96, the spacer 98 having the above-described configuration have uniform thicknesses tb, tc, td, and te measured in directions (indicated by arrows B, C, D, and E) normal to surfaces of the spacer 98, which are in contact with the side surfaces 80B, 80C, 80D, and 80E of the ultrasonic oscillator 80 as illustrated in FIG. 10.

It is preferable that the spacer 98 is made of resin or rubber elastic in a thickness direction corresponding to each normal direction described above, and it is more preferable that the spacer 98 is made of a material such as silicone, which is that same as that of the acoustic lens 90.

[Spacer 110]

As illustrated in FIGS. 8 and 9, a spacer 110 is provided between the bottom surface 80F of the ultrasonic oscillator 80 and the bottom surface 96F of the ultrasonic-oscillator housing part 96.

The spacer 110 includes four spacers 110B, 110C, 110D, and 110E. The spacer 110B supports part of the bottom surface 96F of the ultrasonic-oscillator housing part 96, which corresponds to the side surface 80B of the ultrasonic oscillator 80, the spacer 110C supports part of the bottom surface 96F of the ultrasonic-oscillator housing part 96, which corresponds to the side surface 80C of the ultrasonic oscillator 80, the spacer 110D supports part of the bottom surface 96F of the ultrasonic-oscillator housing part 96, which corresponds to the side surface 80D of the ultrasonic oscillator 80, and the spacer 110E supports part of the bottom surface 96F of the ultrasonic-oscillator housing part 96, which corresponds to the side surface 80E of the ultrasonic oscillator 80. In other words, the spacer 110 is provided in a peripheral part of the bottom surface 80F.

The ultrasonic oscillator 80 is housed in the ultrasonic-oscillator housing part 96 with its distal end being tilted downward, and thus the spacers 110B and 110C are each formed in a triangle, the spacer 110D is formed in a rectangle, and the spacer 110E is formed in a rectangle having a height larger than that of the spacer 110D.

The spacer 110 provides a space 112 in which the wires 94 are to be arranged, between the bottom surface 80F of the ultrasonic oscillator 80 and the bottom surface 96F of the ultrasonic-oscillator housing part 96. The spacers 98 and 110 can prevent melted resin of the acoustic lens 90 from flowing into the space 112 at formation of the acoustic lens 90 to be described later.

Similarly to the spacer 98, it is preferable that the spacer 110 is made of elastic resin or rubber, and it is more preferable that the spacer 110 is made of a material such as silicone, which is the same as that of the acoustic lens 90.

[Acoustic Lens 90]

The acoustic lens 90 covers the observation surface 80A of the ultrasonic oscillator 80 and the spacer 98, and is adhered to the ultrasonic-oscillator housing part 96. A method of assembling the ultrasonic oscillator 80 to the ultrasonic-oscillator housing part 96 will be described later.

<<Endoscope Observation Unit 52>>

The endoscope observation unit 52 includes, for example, an observation optical system 62, illumination optical systems 64 and 66, and an image pickup element (not illustrated), and is provided to the distal end part body 70 on a proximal end side of the ultrasonic observation unit 50, avoiding the surgical-tool guide opening 54.

In the distal end part body 70, tilted surfaces 70a and 70b tilted at a predetermined angle with respect to a plane orthogonal to the longitudinal axis Z are provided at positions closer to the distal end than the surgical-tool guide opening 54 on both sides of the surgical-tool guide opening 54 in the traverse direction. An observation window 62a of the observation optical system 62 and an illumination window 64a of the illumination optical system 64 are arranged on the tilted surface 70a on the left side in the direction from the proximal end side toward the distal end side. An illumination window 66a of the illumination optical system 66 is arranged on the tilted surface 70b on the right side in the direction from the proximal end side toward the distal end side.

The observation optical system 62 includes an optical system member (not illustrated) that takes in light from an object in the observation view range through the observation window 62a and images an object image inside of the distal end rigid part 40. An image pickup element (not illustrated) that captures the object image imaged by the observation optical system 62 and generates an image signal is arranged inside of the distal end rigid part 40.

The illumination optical systems 64 and 66 each include an optical system member that emits illumination light transmitted from the light source device 16 (refer to FIG. 2) through a light guide, to the observation view range through the illumination windows 64a and 66a in a diffusive manner.

A cleaning nozzle 68 that sprays liquid and gas toward the observation window 62a is provided near the observation window 62a on the tilted surface 70a.

<<Surgical-Tool Guide Opening 54>>

The surgical-tool guide opening 54 includes a concave elevation housing part 72 provided on the proximal end side of the ultrasonic observation unit 50 and communicated with an opening 86a of the connecting pipe 86 in FIG. 3. The elevator 74, which changes the direction of guiding the puncture needle 100 guided through the opening 86a of the connecting pipe 86 from the surgical-tool guide opening 54, is rotatably provided to the elevation housing part 72.

The elevator 74 is coupled with a shaft provided to a lever (not illustrated). The lever is rotatably provided to the distal end part body 70 through the shaft and is coupled with a distal end of an operation wire (not illustrated), and a proximal end of the operation wire is coupled with the elevation lever 24b (refer to FIG. 2) of the operating unit 24. With this configuration, when the operation wire is pushed or pulled by operating the elevation lever 24b, the elevator 74 is rotated along with the lever through the shaft so as to change an angle at which the elevator 74 stands up.

Accordingly, the puncture needle 100 guided through the opening 86a of the connecting pipe 86 is guided in a predetermined guide direction along the elevator 74 to the outside through the surgical-tool guide opening 54.

[Method of Assembling the Ultrasonic Oscillator 80 to the Ultrasonic-Oscillator Housing Part 96]

In the present embodiment, after the ultrasonic oscillator 80 to which the acoustic lens 90 is not provided is housed in the ultrasonic-oscillator housing part 96 of the distal end part body 70, the distal end part body 70 is loaded into a mold 114 (refer to FIG. 9), and then fluid melted resin (silicone resin) to be formed into the acoustic lens 90 through solidification is injected into the mold 114.

Figure 11:
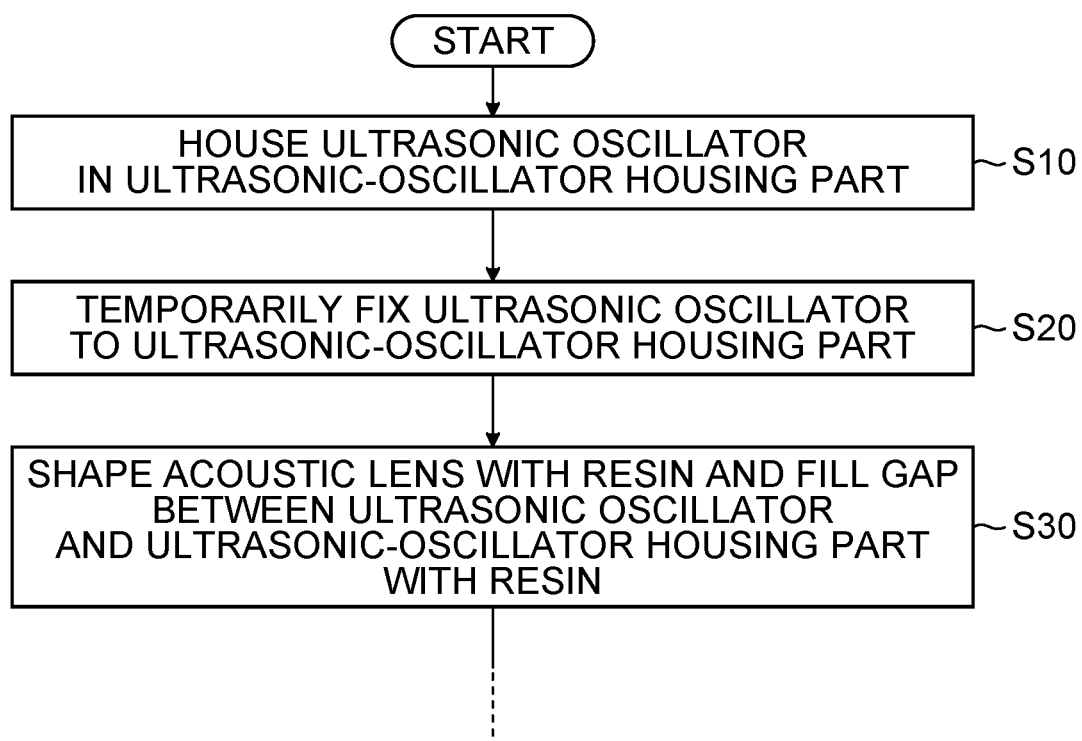
FIG. 11 is a flowchart of a method of manufacturing an ultrasonic endoscope according to the present embodiment.

FIG. 11 is a flowchart of a method of manufacturing the ultrasonic endoscope 10 according to the present embodiment. The method of manufacturing the ultrasonic endoscope 10 according to the present embodiment performs step S10 of housing the ultrasonic oscillator 80 in the ultrasonic-oscillator housing part 96. Next, the method performs step S20 of temporarily fixing the ultrasonic oscillator 80 to the ultrasonic-oscillator housing part 96 while an extended line 54B of a center line 54A of the surgical-tool guide opening 54 is positioned in an observation region 81 of the ultrasonic oscillator 80 as illustrated in FIG. 3. Next, the method performs step S30 of shaping the acoustic lens 90 on the observation surface 80A of the ultrasonic oscillator 80 with fluid resin and filling a gap between the ultrasonic oscillator 80 and the ultrasonic-oscillator housing part 96 with the resin while the ultrasonic oscillator 80 is temporarily fixed.

Specifically, first, the ultrasonic oscillator 80 including the spacers 98 and 110 is housed in the ultrasonic-oscillator housing part 96 of the distal end part body 70 (S10), and then the ultrasonic oscillator 80 is accurately positioned and temporarily fixed to the ultrasonic-oscillator housing part 96 through the spacers 98 and 110 (S20). Next, the distal end part body 70 is fixed inside of the mold 114. Next, melted resin (not illustrated) is injected through an injection opening 116 of the mold 114. Next, the mold 114 is placed into a vacuum chamber (not illustrated) to perform defoaming of the melted resin. After the defoaming, the melted resin is injected into the mold 114 again to fill the inside of the mold 114 with the melted resin (S30). Next, a plurality of molds are bonded to the mold so as to form a mold assembly. Next, the mold assembly is placed into a furnace so as to solidify the melted resin. Thereafter, the mold assembly is taken out of the furnace and separated to obtain the distal end part body 70 out of the mold 114. Lastly, any unnecessary burr around the acoustic lens 90 is removed.

The acoustic lens 90 covering the observation surface 80A of the ultrasonic oscillator 80 and the spacer 98 and adhered to the ultrasonic-oscillator housing part 96 is shaped in this manner. In other words, in the process of providing the acoustic lens 90 to the observation surface 80A of the ultrasonic oscillator 80, the gap between the ultrasonic oscillator 80 and the ultrasonic-oscillator housing part 96 is filled with the resin the acoustic lens 90.

According to the present embodiment, the position of the ultrasonic oscillator 80 can be accurately and easily adjusted through the spacer 98 with respect to the ultrasonic-oscillator housing part 96. Accordingly, in the ultrasonic endoscope 10 according to the present embodiment, the position of the ultrasonic oscillator 80 can be accurately and easily adjusted with respect to the surgical-tool guide opening 54. Thus, the ultrasonic endoscope 10 according to the present embodiment allows the puncture needle 100 as a surgical tool to be accurately guided into the ultrasonic observation region, thereby achieving a favorable ultrasonic observation.

The acoustic lens 90 according to the present embodiment covers the observation surface 80A of the ultrasonic oscillator 80 and the spacer 98 and is adhered to the ultrasonic-oscillator housing part 96. In other words, the gap between the ultrasonic oscillator 80 and the ultrasonic-oscillator housing part 96 is sealed by part of the acoustic lens 90 without using sealing agent. The part of the acoustic lens 90 provides enhanced water-tightness of the ultrasonic observation unit 50 against the distal end part body 70.

[Effect of the Spacers 98 and 110]

The spacer 98 has the uniform thicknesses tb, tc, td, and te measured in the directions (indicated by arrows B, C, D, and E) normal to the surfaces of the spacer 98, which are in contact with the side surfaces 80B, 80C, 80D, and 80E of the ultrasonic oscillator 80 as illustrated in FIG. 10, when the ultrasonic oscillator 80 is housed in the ultrasonic-oscillator housing part 96. With this configuration, the ultrasonic oscillator 80 can be highly accurately housed in the ultrasonic-oscillator housing part 96.

Since the spacer 98 includes at least one spacer of the spacers 98B and 98C in contact with the side surfaces 80B and 80C, a constant gap can be held through at least one spacer between the ultrasonic-oscillator housing part 96 and at least one side surface of the side surfaces 80B to 80E of the ultrasonic oscillator 80, which is parallel to the longitudinal axis Z of the insertion unit 22.

In addition, since the spacer 98 includes the two spacers 98B and 98C in contact with the side surfaces 80B and 80C, a constant gap can be held through the spacers 98B and 98C between the ultrasonic-oscillator housing part 96 and the side surfaces 80B and 80C parallel to the longitudinal axis Z of the insertion unit 22 among the side surfaces 80B to 80E of the ultrasonic oscillator 80.

In addition, in the above-described embodiment, it is preferable that the spacers 98B and 98C provided between the side surfaces 80B and 80C of the ultrasonic oscillator 80 and the side surfaces 96B and 96C of the ultrasonic-oscillator housing part 96 have thicknesses tb and tc equal to each other, each thickness being measured in a direction (illustrated by arrow B or C) normal to a surface of the spacer 98B or 98C, which is in contact with the corresponding side surface 80B or 80C of the ultrasonic oscillator 80. With this configuration, the two side surfaces 80B and 80C parallel to the longitudinal axis Z of the insertion unit 22 and facing to each other among the side surfaces 80B to 80E of the ultrasonic oscillator 80 can be arranged in parallel to the longitudinal axis Z of the insertion unit 22 through the spacers 98B and 98C.

In addition, it is preferable that the spacer 98 is provided between the side surfaces 80D and 80E intersecting with the longitudinal axis Z of the insertion unit 22 among the side surfaces 80B to 80E of the ultrasonic oscillator 80 and the side surfaces 96D and 96E of the ultrasonic-oscillator housing part 96. Thus, it is preferable that the spacer 98 includes at least one spacer of the spacers 98D and 98E in contact with the side surfaces 80D and 80E. With this configuration, a constant gap can be held through the spacer between the ultrasonic-oscillator housing part 96 and at least one side surface intersecting with the longitudinal axis Z of the insertion unit 22 among the side surfaces of the ultrasonic oscillator.

In addition, it is preferable that the spacer 98 is provided between the two side surfaces 80D and 80E intersecting with the longitudinal axis Z of the insertion unit 22 and facing to each other among the side surfaces 80B to 80E of the ultrasonic oscillator 80 and the side surfaces 96D and 96E of the ultrasonic-oscillator housing part 96. In other words, it is preferable that the spacer 98 includes the two spacers 98D and 98E in contact with the side surfaces 80D and 80E. With this configuration, a constant gap can be held through the spacers 98D and 98E between the ultrasonic-oscillator housing part 96 and the side surfaces 80D and 80E intersecting with the longitudinal axis Z of the insertion unit 22 among the side surfaces of the ultrasonic oscillator 80.

In the above-described embodiment, it is preferable that the spacers 98D and 98E provided between the two side surfaces 80D and 80E and the side surfaces 96D and 96E of the ultrasonic-oscillator housing part 96 have thicknesses td and te equal to each other, each being measured in a direction (illustrated by arrow D or E) normal to a surface of the spacer 98D or 98E, which is in contact with a corresponding one of the side surface 80D or 80E of the ultrasonic oscillator 80. With this configuration, the two side surfaces 80D and 80E intersecting with the longitudinal axis Z of the insertion unit 22 and facing to each other among the side surfaces 80B to 80E of the ultrasonic oscillator 80 can be arranged in a direction intersecting with the longitudinal axis Z of the insertion unit 22 through the spacers 98D and 98E.

In addition, since the spacer 98 is made of resin or rubber elastic in the thickness direction corresponding to the above-described normal direction, any error in the dimensions of the ultrasonic oscillator 80 and the ultrasonic-oscillator housing part 96 can be canceled through elastic deformation of the spacer 98.

In addition, it is preferable that the spacer 110 is provided between the bottom surface 80F of the ultrasonic oscillator 80 and the ultrasonic-oscillator housing part 96. With this configuration, the bottom surface 80F of the ultrasonic oscillator 80 can be supported with respect to the ultrasonic-oscillator housing part 96 through the spacer 110.

In addition, in the present embodiment, it is preferable that the wiring connection unit 92 is provided in the central part of the bottom surface 80F of the ultrasonic oscillator 80, and the spacer 110 is provided in the peripheral part of the bottom surface 80F. With this configuration, the spacer 110 serves as a weir, thereby preventing melted resin of the acoustic lens 90 from flowing into the space 112 in which the wires 94 are arranged when the acoustic lens 90 is shaped.

In addition, since the spacer 110 is made of elastic resin or rubber, any error in the dimensions of the ultrasonic oscillator 80 and the ultrasonic-oscillator housing part 96 can be canceled through elastic deformation of the spacer 110.

In the above-described embodiment, the spacers 98 and 110 are provided between the ultrasonic oscillator 80 and the ultrasonic-oscillator housing part 96, but in place of the spacers 98 and 110, protrusions may be provided to at least one of the ultrasonic oscillator 80 and the ultrasonic-oscillator housing part 96.

Description of the configuration in which protrusions are provided in place of the spacers 98 and 110 is equivalent to the above description with the spacers 98 and 110 being replaced with protrusions. The same effect as that of the spacers 98 and 110 is obtained.

The following describes the configuration in which protrusions are provided and the effect thereof, including duplicate description equivalent to the above description.

[Configuration in which Protrusions are Provided]

Figure 12:
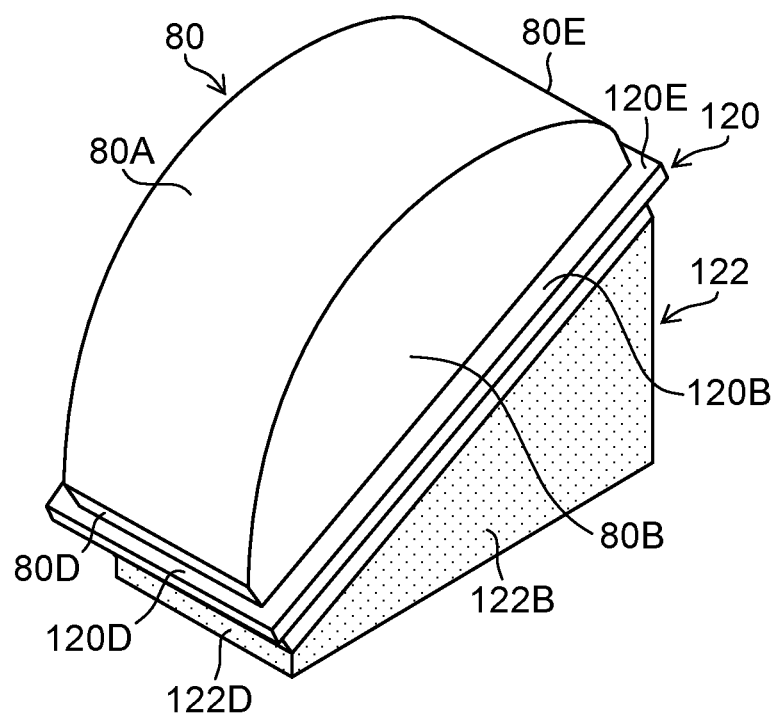
FIG. 12 is a perspective view of the ultrasonic oscillator, illustrating positioning of the ultrasonic oscillator with respect to the ultrasonic-oscillator housing part through protrusions.
Figure 13:
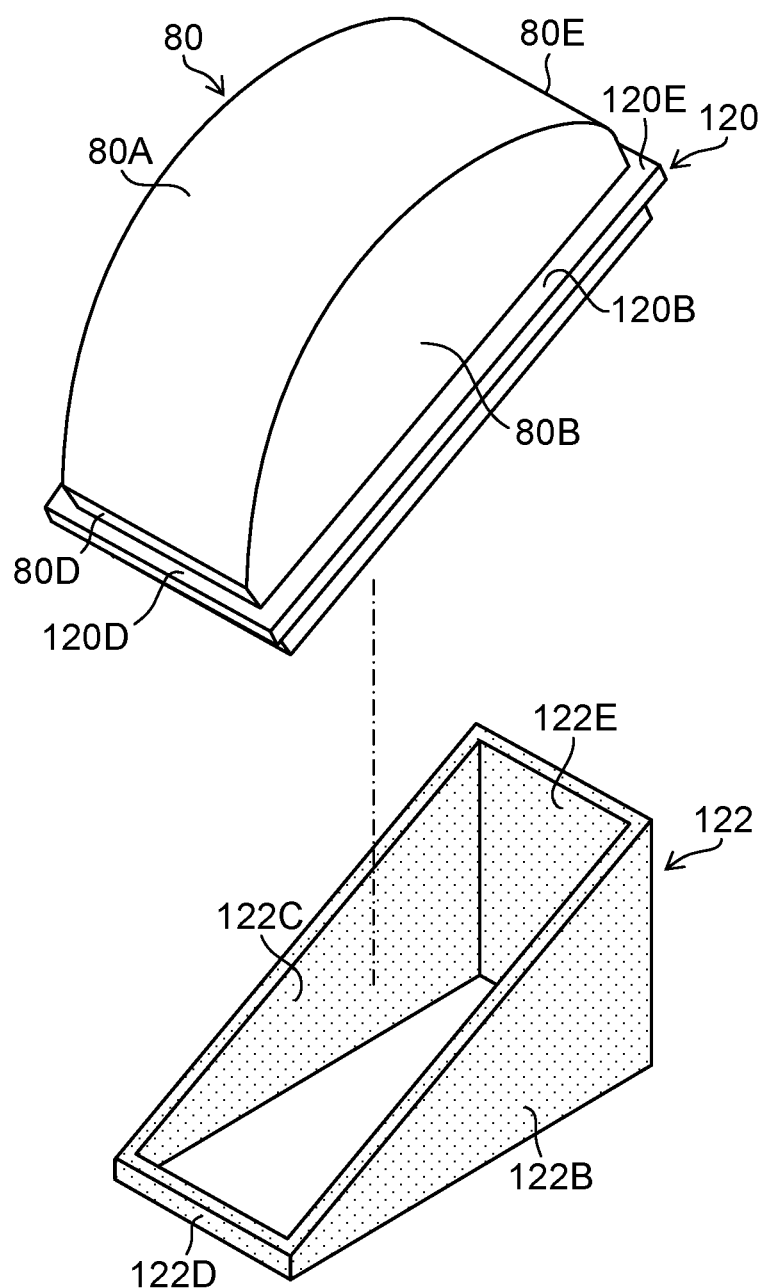
FIG. 13 is an exploded view of the ultrasonic oscillator in FIG. 12.
Figure 14:
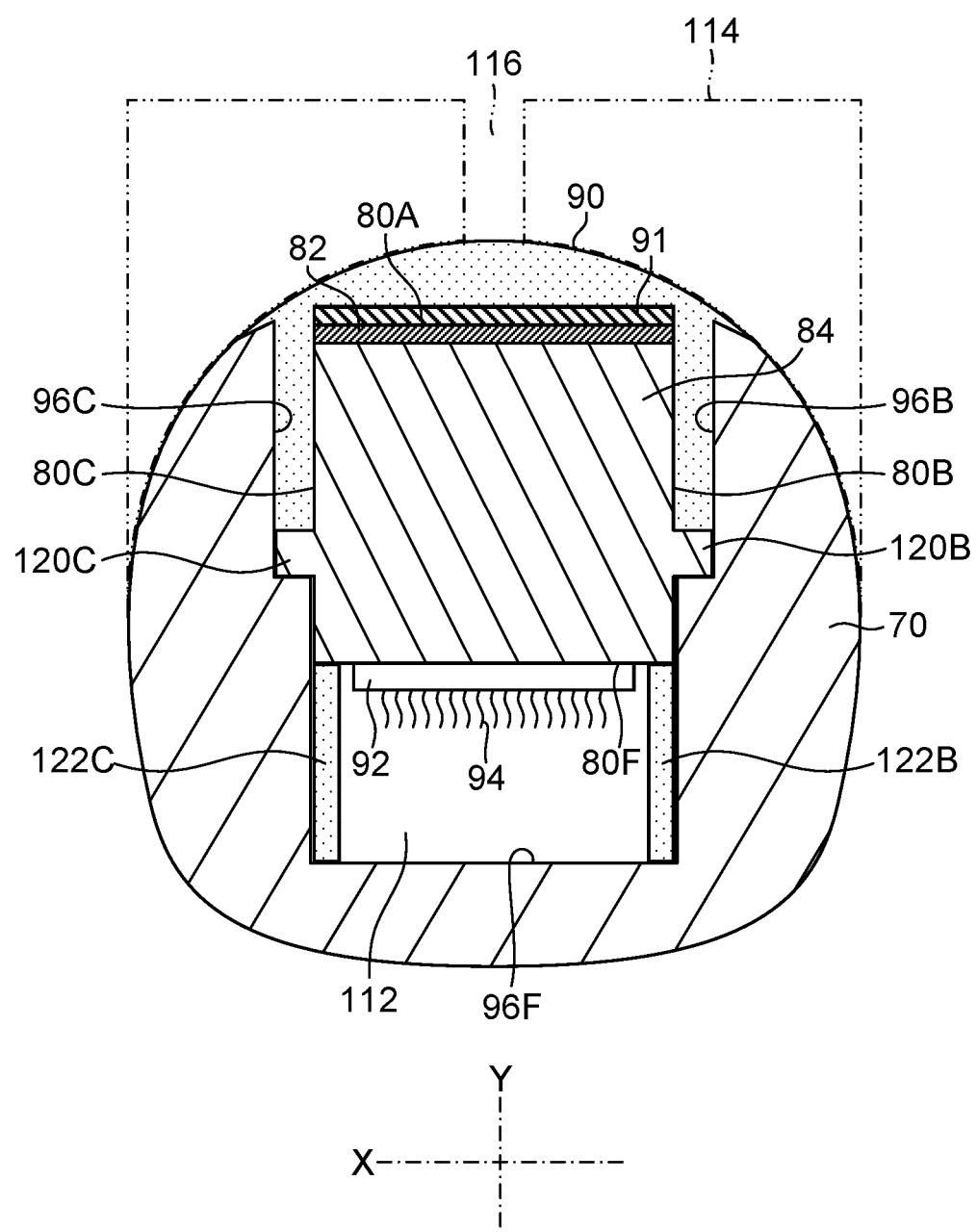
FIG. 14 is a sectional view of the distal end part body including the ultrasonic oscillator in FIG. 12.

FIGS. 12, 13, and 14 are a perspective view of the ultrasonic oscillator 80, an exploded view of the ultrasonic oscillator 80, and a sectional view of the distal end part body 70, respectively, illustrating positioning of the ultrasonic oscillator 80 with respect to the ultrasonic-oscillator housing part 96 through protrusions 120 and 122 in place of spacers.

A protrusion 120B of the protrusion 120 is provided on the side surface 80B of the ultrasonic oscillator 80, and has a function equivalent to that of the spacer 98B of the spacer 98 illustrated in FIGS. 8 to 10.

A protrusion 120C of the protrusion 120 is provided on the side surface 80C of the ultrasonic oscillator 80, and has a function equivalent to that of the spacer 98C of the spacer 98.

A protrusion 120D of the protrusion 120 is provided on the side surface 80D of the ultrasonic oscillator 80, and has a function equivalent to that of the spacer 98D of the spacer 98.

A protrusion 120E of the protrusion 120 is provided on the side surface 80E of the ultrasonic oscillator 80, and has a function equivalent to that of the spacer 98E of the spacer 98.

A protrusion 122B of the protrusion 122 has a function equivalent to that of the spacer 110B of the spacer 110 illustrated in FIG. 8, a protrusion 122C of the protrusion 122 has a function equivalent to that of the spacer 110C of the spacer 110, a protrusion 122D of the protrusion 122 has a function equivalent to that of the spacer 110D of the spacer 110, and a protrusion 122E of the protrusion 122 has a function equivalent to that of the spacer 110E of the spacer 110. These protrusions 120 and 122 are formed integrally with the ultrasonic oscillator 80, but may be provided to the ultrasonic-oscillator housing part 96.

Thus, the configuration with the protrusions 120 and 122 illustrated in FIGS. 12 to 14 achieves the same effect as that of the configuration with the spacers 98 and 110 illustrated in FIGS. 8 to 10.

In other words, the protrusion 120 has a uniform thickness in a direction normal to a surface of the protrusion 120, which is in contact with a corresponding one of the side surfaces 80B, 80C, 80D, and 80E of the ultrasonic oscillator 80, when the ultrasonic oscillator 80 is housed in the ultrasonic-oscillator housing part 96. With this configuration, the ultrasonic oscillator 80 can be accurately housed in the ultrasonic-oscillator housing part 96.

Since the protrusion 120 includes at least one protrusion of the protrusions 120B and 120C in contact with the side surface 80B as a first side surface and the side surface 80C as a second side surface, a constant gap can be held through the protrusion between the ultrasonic-oscillator housing part 96 and at least one side surface parallel to the longitudinal axis Z of the insertion unit 22 among the side surfaces of the ultrasonic oscillator 80.

In addition, since the protrusion 120 includes the two protrusions 120B and 120C in contact with the side surfaces 80B and 80C, a constant gap can be held through the protrusions 120B and 120C between the ultrasonic-oscillator housing part 96 and the side surfaces 80B and 80C parallel to the longitudinal axis Z of the insertion unit 22 among the side surfaces of the ultrasonic oscillator 80.

In addition, in the above-described embodiment, it is preferable that the protrusions 120B and 120C provided between the side surfaces 80B and 80C of the ultrasonic oscillator 80 and the side surfaces 96B and 96C of the ultrasonic-oscillator housing part 96 have thicknesses equal to each other, each thickness being measured in a direction normal to a surface of the protrusion 120B or 120C, which is in contact with a corresponding one of the side surface 80B or 80C of the ultrasonic oscillator 80. With this configuration, the two side surfaces 80B and 80C parallel to the longitudinal axis Z of the insertion unit 22 and facing to each other among the side surfaces of the ultrasonic oscillator 80 can be arranged in parallel to the longitudinal axis Z of the insertion unit 22 through the protrusions 120B and 120C.

In addition, it is preferable that the protrusion 120 is provided between the side surfaces 96D and 96E of the ultrasonic-oscillator housing part 96 and the side surface 80D as a third side surface and the side surface 80E as a fourth side surface intersecting with the longitudinal axis Z of the insertion unit 22 among the side surfaces 80B to 80E of the ultrasonic oscillator 80. In other words, it is preferable that the protrusion 120 includes at least one protrusion of the protrusions 120D and 120E in contact with the side surfaces 80D and 80E. With this configuration, a constant gap can be held through the protrusion between the ultrasonic-oscillator housing part 96 and at least one side surface intersecting with the longitudinal axis Z of the insertion unit 22 among the side surfaces 80B to 80E of the ultrasonic oscillator 80.

In addition, it is preferable that the protrusion 120 is provided between the side surfaces 96D and 96E of the ultrasonic-oscillator housing part 96 and the two side surfaces 80D and 80E intersecting with the longitudinal axis Z of the insertion unit 22 and facing to each other among the side surfaces 80B to 80E of the ultrasonic oscillator 80. In other words, it is preferable that the protrusion 120 includes the two protrusions 120D and 120E in contact with the side surfaces 80D and 80E. With this configuration, a constant gap can be held through the protrusions 120D and 120E between the ultrasonic-oscillator housing part 96 and the side surfaces 80D and 80E intersecting with the longitudinal axis Z of the insertion unit 22 among the side surfaces 80B to 80E of the ultrasonic oscillator 80.

In the above-described embodiment, it is preferable that the protrusions 120D and 120E provided between the two side surfaces 80D and 80E and the side surfaces 96D and 96E of the ultrasonic-oscillator housing part 96 have thicknesses equal to each other, each thickness being measured in a direction normal to a surface of the protrusion 120D or 120E, which is in contact with a corresponding one of the side surface 80D or 80E of the ultrasonic oscillator 80. With this configuration, the two side surfaces 80D and 80E intersecting with the longitudinal axis Z of the insertion unit 22 and facing to each other among the side surfaces 80B to 80E of the ultrasonic oscillator 80 can be arranged in a direction intersecting with the longitudinal axis Z of the insertion unit 22 through the protrusions 120D and 120E.

In addition, since the protrusion 120 is made of resin or rubber elastic in the thickness direction corresponding to the above-described normal direction, any error in the dimensions of the ultrasonic oscillator 80 and the ultrasonic-oscillator housing part 96 can be canceled through elastic deformation of the protrusion 120.

In addition, it is preferable that the protrusion 122 is provided between the bottom surface 80F of the ultrasonic oscillator 80 and the ultrasonic-oscillator housing part 96.

With this configuration, the bottom surface 80F of the ultrasonic oscillator 80 can be supported with respect to the ultrasonic-oscillator housing part 96 through the protrusion 122.

In addition, in the present embodiment, it is preferable that the wiring connection unit 92 is provided in the central part of the bottom surface 80F of the ultrasonic oscillator 80, and the protrusion 122 is provided in the peripheral part of the bottom surface 80F. With this configuration, the protrusion 122 serves as a weir, thereby preventing melted resin of the acoustic lens 90 from flowing into the space 112 in which the wires 94 are arranged when the acoustic lens 90 is shaped.

In addition, since the protrusion 122 is made of elastic resin or rubber, any error in the dimensions of the ultrasonic oscillator 80 and the ultrasonic-oscillator housing part 96 can be canceled through elastic deformation of the protrusion 122.

A preferable uniform thickness of the spacer 98 or the protrusion 120 is a uniform thickness that provides parallelism enough to keep, inside the ultrasonic observation region, the puncture needle 100 guided through the guide opening 54 and entering into the ultrasonic observation region of the ultrasonic oscillator 80 from a proximal end face of the observation region. The ultrasonic observation region when viewed from the guide opening 54 includes a region narrowed in a direction intersecting with the longitudinal axis of the insertion unit 22. The uniform thickness that provides parallelism enough to keep the puncture needle 100 inside the ultrasonic observation region through the spacer 98 or the protrusion 120 is such a uniform thickness that the parallelism of the side surfaces 80B and 80C, which are parallel to the longitudinal axis of the insertion unit 22 among the side surfaces of the ultrasonic oscillator 80, with respect to the guide direction of the puncture needle 100 can be provided through the spacer 98 or the protrusion 120 so as to keep the puncture needle 100 inside the narrowed region.

The thickness of the spacer 98 or the protrusion 120 in the normal direction is a thickness that achieves electrical insulation through the spacer 98 or the protrusion 120 and a small outer shape of the distal end part body 70. Thicknesses in the normal direction are said to be equal to each other with any variation in manufacturing the spacer 98 or the protrusion 120.

What is claimed is:
1. An ultrasonic endoscope comprising:
   an insertion tube inserted into an inside of a body;
   a distal tip provided to a distal end of the insertion tube and provided with a surgical-tool guide opening;
   an ultrasonic probe provided to the distal tip;
   an ultrasonic oscillator provided to the ultrasonic probe and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element;
   an ultrasonic-oscillator housing part provided to the distal tip, covering the side surfaces and the bottom surface of the ultrasonic oscillator, and housing the ultrasonic oscillator;
   spacers provided between the ultrasonic oscillator and the ultrasonic-oscillator housing part; and an acoustic lens covering the observation surface of the ultrasonic oscillator and the spacers, and adhered to the ultrasonic-oscillator housing part, wherein the spacers have a uniform thickness in a direction normal to a surface of the spacers, which are in contact with a corresponding one of the side surfaces of the ultrasonic oscillator when the ultrasonic oscillator is housed in the ultrasonic-oscillator housing part, wherein the spacers are provided between the ultrasonic-oscillator housing part and a side surface parallel to a longitudinal axis of the insertion tube among the side surfaces of the ultrasonic oscillator, wherein the spacers are provided between the ultrasonic-oscillator housing part and two side surfaces parallel to the longitudinal axis of the insertion tube and facing to each other among the side surfaces of the ultrasonic oscillator, and wherein when the ultrasonic oscillator is housed in the ultrasonic-oscillator housing part, the spacers provided between the ultrasonic-oscillator housing part and the two side surfaces have thicknesses equal to each other, each thickness being measured in a direction normal to a surface of the spacers, which are in contact with a corresponding one of the side surfaces of the ultrasonic oscillator.

2. The ultrasonic endoscope according to claim 1, wherein the spacers are provided between the ultrasonic-oscillator housing part and a side surface intersecting with the longitudinal axis of the insertion tube among the side surfaces of the ultrasonic oscillator.

3. The ultrasonic endoscope according to claim 1, wherein the spacers are elastic in a thickness direction corresponding to a normal direction.

4. The ultrasonic endoscope according to claim 1, wherein the spacers are provided between the ultrasonic-oscillator housing part and the bottom surface of the ultrasonic oscillator.

5. The ultrasonic endoscope according to claim 4, further comprising a wiring connector provided to the ultrasonic oscillator and connected with wiring for supplying a drive voltage to the ultrasonic oscillator,
wherein the wiring connector is provided in a central area of the bottom surface, and the spacers are provided in a peripheral area of the bottom surface.

6. An ultrasonic endoscope comprising:
an insertion tube inserted into an inside of a body;
a distal tip provided to a distal end of the insertion tube and provided with a surgical-tool guide opening;
an ultrasonic probe provided to the distal tip;
an ultrasonic oscillator provided to the ultrasonic probe and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element;
an ultrasonic-oscillator housing part provided to the distal tip, covering the side surfaces and the bottom surface of the ultrasonic oscillator, and housing the ultrasonic oscillator;
spacers provided between the ultrasonic oscillator and the ultrasonic-oscillator housing part; and
an acoustic lens covering the observation surface of the ultrasonic oscillator and the spacers, and adhered to the ultrasonic-oscillator housing part,
wherein the spacers have a uniform thickness in a direction normal to a surface of the spacers, which are in contact with a corresponding one of the side surfaces of the ultrasonic oscillator when the ultrasonic oscillator is housed in the ultrasonic-oscillator housing part,
wherein the spacers are provided between the ultrasonic-oscillator housing part and a side surface intersecting with the longitudinal axis of the insertion tube among the side surfaces of the ultrasonic oscillator,
wherein the spacers are provided between the ultrasonic-oscillator housing part and two side surfaces intersecting with the longitudinal axis of the insertion tube and facing to each other among the side surfaces of the ultrasonic oscillator, and
wherein when the ultrasonic oscillator is housed in the ultrasonic-oscillator housing part, the spacers provided between the ultrasonic-oscillator housing part and the two side surfaces have thicknesses equal to each other, each thickness being measured in a direction normal to a surface of the spacers, which are in contact with a corresponding one of the side surfaces of the ultrasonic oscillator.

7. An ultrasonic endoscope comprising:
an insertion tube inserted into an inside of a body;
a distal tip provided to a distal end of the insertion tube and provided with a surgical-tool guide opening;
an ultrasonic probe provided to the distal tip;
an ultrasonic oscillator provided to the ultrasonic probe and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element;
an ultrasonic-oscillator housing part provided to the distal tip, covering the side surfaces and the bottom surface of the ultrasonic oscillator, and housing the ultrasonic oscillator;
a protrusion provided to at least one of the ultrasonic oscillator and the ultrasonic-oscillator housing part; and
an acoustic lens covering the observation surface of the ultrasonic oscillator and the protrusion and adhered to the ultrasonic-oscillator housing part,
wherein the protrusion has a uniform thickness in a direction normal to a surface of the protrusion, which is in contact with a corresponding one of the side surfaces of the ultrasonic oscillator when the ultrasonic oscillator is housed in the ultrasonic-oscillator housing part,
wherein the protrusion is provided between the ultrasonic-oscillator housing part and a side surface parallel to a longitudinal axis of the insertion tube among the side surfaces of the ultrasonic oscillator;
wherein the protrusion is provided to at least one of the ultrasonic-oscillator housing part and a first side surface as one of two side surfaces parallel to the longitudinal axis of the insertion tube and facing to each other among the side surfaces of the ultrasonic oscillator, and is provided to at least one of the ultrasonic-oscillator housing part and a second side surface as the other side surface, and
wherein when the ultrasonic oscillator is housed in the ultrasonic-oscillator housing part, the protrusion provided to at least one of the ultrasonic-oscillator housing part and the first side surface and the protrusion provided to at least one of the ultrasonic-oscillator housing part and the second side surface have thicknesses equal to each other, each thickness being measured in a direction normal to a surface of the protrusion, which is in contact with a corresponding one of the first side surface and the second side surface of the ultrasonic oscillator.

8. The ultrasonic endoscope according to claim 7, wherein the protrusion is provided to at least one of the ultrasonic-oscillator housing part and a side surface intersecting with the longitudinal axis of the insertion tube among the side surfaces of the ultrasonic oscillator.

9. The ultrasonic endoscope according to claim 7, wherein the protrusion is elastic in a thickness direction corresponding to a normal direction.

10. The ultrasonic endoscope according to claim 7, wherein the protrusion is provided to at least one of the ultrasonic-oscillator housing part and the bottom surface of the ultrasonic oscillator.

11. The ultrasonic endoscope according to claim 10, further comprising a wiring connector provided to the ultrasonic oscillator and connected with wiring for supplying a drive voltage to the ultrasonic oscillator,
wherein the wiring connector is provided in a central area of the bottom surface, and the protrusion is provided in a peripheral area of the bottom surface.

12. An ultrasonic endoscope comprising:
an insertion tube inserted into an inside of a body;
a distal tip provided to a distal end of the insertion tube and provided with a surgical-tool guide opening;
an ultrasonic probe provided to the distal tip;
an ultrasonic oscillator provided to the ultrasonic probe and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element;
an ultrasonic-oscillator housing part provided to the distal tip, covering the side surfaces and the bottom surface of the ultrasonic oscillator, and housing the ultrasonic oscillator;
a protrusion provided to at least one of the ultrasonic oscillator and the ultrasonic-oscillator housing part; and
an acoustic lens covering the observation surface of the ultrasonic oscillator and the protrusion and adhered to the ultrasonic-oscillator housing part,
wherein the protrusion has a uniform thickness in a direction normal to a surface of the protrusion, which is in contact with a corresponding one of the side surfaces of the ultrasonic oscillator when the ultrasonic oscillator is housed in the ultrasonic-oscillator housing part,
wherein the protrusion is provided to at least one of the ultrasonic-oscillator housing part and a side surface intersecting with the longitudinal axis of the insertion tube among the side surfaces of the ultrasonic oscillator,
wherein the protrusion is provided to at least one of the ultrasonic-oscillator housing part and a third side surface as one of two side surfaces intersecting with the longitudinal axis of the insertion tube and facing to each other among the side surfaces of the ultrasonic oscillator, and is provided to at least one of the ultrasonic-oscillator housing part and a fourth side surface as the other side surface, and
wherein when the ultrasonic oscillator is housed in the ultrasonic-oscillator housing part, the protrusion provided to at least one of the ultrasonic-oscillator housing part and the third side surface and the protrusion provided to at least one of the ultrasonic-oscillator housing part and the fourth side surface have thicknesses equal to each other, each thickness being measured in a direction normal to a surface of the protrusion, which is in contact with a corresponding one of the second side surface and the third side surface of the ultrasonic oscillator.

13. A method of manufacturing an ultrasonic endoscope including an insertion tube inserted into an inside of a body, a distal tip provided to a distal end of the insertion tube and provided with a surgical-tool guide opening, an ultrasonic probe provided to the distal tip, an ultrasonic oscillator provided to the ultrasonic probe and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element, and an ultrasonic-oscillator housing part provided to the distal tip and housing the ultrasonic oscillator, the method comprising:
housing the ultrasonic oscillator in the ultrasonic-oscillator housing part;
temporarily fixing the ultrasonic oscillator to the ultrasonic-oscillator housing part by providing spacers between the ultrasonic oscillator and the ultrasonic-oscillator housing part while an extended line of a center line of the surgical-tool guide opening is positioned in an observation region of the ultrasonic oscillator; and
shaping an acoustic lens on the observation surface of the ultrasonic oscillator with fluid resin and filling a gap between the ultrasonic oscillator and the ultrasonic-oscillator housing part with the resin while temporarily fixing the ultrasonic oscillator with the spacers, wherein:
the spacers have a uniform thickness in a direction normal to a surface of the spacers, which are in contact with a corresponding one of the side surfaces of the ultrasonic oscillator when the ultrasonic oscillator is housed in the ultrasonic-oscillator housing part,
the spacers are provided between the ultrasonic-oscillator housing part and a side surface parallel to a longitudinal axis of the insertion tube among the side surfaces of the ultrasonic oscillator,
the spacers are provided between the ultrasonic-oscillator housing part and two side surfaces parallel to the longitudinal axis of the insertion tube and facing to each other among the side surfaces of the ultrasonic oscillator, and
when the ultrasonic oscillator is housed in the ultrasonic-oscillator housing part, the spacers provided between the ultrasonic-oscillator housing part and the two side surfaces have thicknesses equal to each other, each thickness being measured in a direction normal to a surface of the spacers, which are in contact with a corresponding one of the side surfaces of the ultrasonic oscillator.

14. A method of manufacturing an ultrasonic endoscope including an insertion tube inserted into an inside of a body, a distal tip provided to a distal end of the insertion tube and provided with a surgical-tool guide opening, an ultrasonic probe provided to the distal tip, an ultrasonic oscillator provided to the ultrasonic probe and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element, and an ultrasonic-oscillator housing part provided to the distal tip and housing the ultrasonic oscillator, the method comprising:

housing the ultrasonic oscillator in the ultrasonic-oscillator housing part;

temporarily fixing the ultrasonic oscillator to the ultrasonic-oscillator housing part by providing spacers between the ultrasonic oscillator and the ultrasonic-oscillator housing part while an extended line of a center line of the surgical-tool guide opening is positioned in an observation region of the ultrasonic oscillator; and shaping an acoustic lens on the observation surface of the ultrasonic oscillator with fluid resin and filling a gap between the ultrasonic oscillator and the ultrasonic-oscillator housing part with the resin while temporarily fixing the ultrasonic oscillator with the spacers, wherein the spacers have a uniform thickness in a direction normal to a surface of the spacers, which are in contact with a corresponding one of the side surfaces of the ultrasonic oscillator when the ultrasonic oscillator is housed in the ultrasonic-oscillator housing part, the spacers are provided between the ultrasonic-oscillator housing part and a side surface intersecting with the longitudinal axis of the insertion tube among the side surfaces of the ultrasonic oscillator, the spacers are provided between the ultrasonic-oscillator housing part and two side surfaces intersecting with the longitudinal axis of the insertion tube and facing to each other among the side surfaces of the ultrasonic oscillator, and when the ultrasonic oscillator is housed in the ultrasonic-oscillator housing part, the spacers provided between the ultrasonic-oscillator housing part and the two side surfaces have thicknesses equal to each other, each thickness being measured in a direction normal to a surface of the spacers, which is in contact with a corresponding one of the side surfaces of the ultrasonic oscillator.

15. A method of manufacturing an ultrasonic endoscope including an insertion tube inserted into an inside of a body, a distal end part body provided to a distal end of the insertion tube and provided with a surgical-tool guide opening, an ultrasonic observation unit provided to the distal end part body, an ultrasonic oscillator provided to the ultrasonic observation unit and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element, and an ultrasonic-oscillator housing part provided to the distal end part body and housing the ultrasonic oscillator, the method comprising:

housing the ultrasonic oscillator in the ultrasonic-oscillator housing part;

temporarily fixing the ultrasonic oscillator to the ultrasonic-oscillator housing part with a protrusion which is provided to at least one of the ultrasonic oscillator and the ultrasonic-oscillator housing between the ultrasonic oscillator and the ultrasonic-oscillator housing part while an extended line of a center line of the surgical-tool guide opening is positioned in an observation region of the ultrasonic oscillator; and shaping an acoustic lens on the observation surface of the ultrasonic oscillator with fluid resin and filling a gap between the ultrasonic oscillator and the ultrasonic-oscillator housing part with the resin while temporarily fixing the ultrasonic oscillator with the protrusion, wherein the protrusion has a uniform thickness in a direction normal to a surface of the protrusion, which is in contact with a corresponding one of the side surfaces of the ultrasonic oscillator when the ultrasonic oscillator is housed in the ultrasonic-oscillator housing part, the protrusion is provided between the ultrasonic-oscillator housing part and a side surface parallel to a longitudinal axis of the insertion tube among the side surfaces of the ultrasonic oscillator, the protrusion is provided to at least one of the ultrasonic-oscillator housing part and a first side surface as one of two side surfaces parallel to the longitudinal axis of the insertion tube and facing to each other among the side surfaces of the ultrasonic oscillator, and is provided to at least one of the ultrasonic-oscillator housing part and a second side surface as the other side surface, and when the ultrasonic oscillator is housed in the ultrasonic-oscillator housing part, the protrusion provided to at least one of the ultrasonic-oscillator housing part and the first side surface and the protrusion provided to at least one of the ultrasonic-oscillator housing part and the second side surface have thicknesses equal to each other, each thickness being measured in a direction normal to a surface of the protrusion, which is in contact with a corresponding one of the first side surface and the second side surface of the ultrasonic oscillator.

16. A method of manufacturing an ultrasonic endoscope including an insertion tube inserted into an inside of a body, a distal tip provided to a distal end of the insertion tube and provided with a surgical-tool guide opening, an ultrasonic probe provided to the distal tip, an ultrasonic oscillator provided to the ultrasonic probe and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element, and an ultrasonic-oscillator housing part provided to the distal tip and housing the ultrasonic oscillator, the method comprising:

housing the ultrasonic oscillator in the ultrasonic-oscillator housing part;

temporarily fixing the ultrasonic oscillator to the ultrasonic-oscillator housing part with a protrusion which is provided to at least one of the ultrasonic oscillator and the ultrasonic-oscillator housing between the ultrasonic oscillator and the ultrasonic-oscillator housing part while an extended line of a center line of the surgical-tool guide opening is positioned in an observation region of the ultrasonic oscillator; and shaping an acoustic lens on the observation surface of the ultrasonic oscillator with fluid resin and filling a gap between the ultrasonic oscillator and the ultrasonic-oscillator housing part with the resin while temporarily fixing the ultrasonic oscillator with the protrusion, wherein the protrusion has a uniform thickness in a direction normal to a surface of the protrusion, which is in contact with a corresponding one of the side surfaces of the ultrasonic oscillator when the ultrasonic oscillator is housed in the ultrasonic-oscillator housing part, the protrusion is provided to at least one of the ultrasonic-oscillator housing part and a side surface intersecting with the longitudinal axis of the insertion tube among the side surfaces of the ultrasonic oscillator, the protrusion is provided to at least one of the ultrasonic-oscillator housing part and a third side surface as one of two side surfaces intersecting with the longitudinal axis of the insertion tube and facing to each other among the side surfaces of the ultrasonic oscillator, and is provided to at least one of the ultrasonic-oscillator housing part and a fourth side surface as the other side surface, and when the ultrasonic oscillator is housed in the ultrasonic-oscillator housing part, the protrusion provided to at least one of the ultrasonic-oscillator housing part and the third side surface and the protrusion provided to at least one of the ultrasonic-oscillator housing part and the fourth side surface have thicknesses equal to each other, each thickness being measured in a direction normal to a surface of the protrusion, which is in contact with a corresponding one of the second side surface and the third side surface of the ultrasonic oscillator.

* * * * *